United States Patent
Kito et al.

(10) Patent No.: US 7,896,547 B2
(45) Date of Patent: Mar. 1, 2011

(54) RADIATION IMAGE CAPTURING SYSTEM

(75) Inventors: Eiichi Kito, Minami-ashigara (JP);
Naoyuki Nishino, Minami-ashigara (JP);
Yasunori Ohta, Yokohama (JP);
Tsuyoshi Tanabe, Odawara (JP);
Takuya Yoshimi, Yokohama (JP);
Takeshi Kuwabara, Minami-ashigara (JP); Kazuharu Ueta, Tokyo (JP);
Makoto Iriuchijima, Gunma-ken (JP)

(73) Assignee: FUJIFILM Corporation, Tokyo (JP)

( * ) Notice: Subject to any disclaimer, the term of this patent is extended or adjusted under 35 U.S.C. 154(b) by 13 days.

(21) Appl. No.: 12/432,889

(22) Filed: Apr. 30, 2009

(65) Prior Publication Data

US 2009/0257564 A1 Oct. 15, 2009

Related U.S. Application Data

(63) Continuation-in-part of application No. 12/179,740, filed on Jul. 25, 2008, now Pat. No. 7,545,914.

(30) Foreign Application Priority Data

| Jul. 27, 2007 | (JP) | ................................ 2007-195935 |
| Feb. 26, 2008 | (JP) | ................................ 2008-044366 |
| Jun. 9, 2008 | (JP) | ................................ 2008-150345 |

(51) Int. Cl.
*A61B 6/08* (2006.01)
(52) U.S. Cl. ........................................ 378/205; 378/207
(58) Field of Classification Search ........... 378/205–206
See application file for complete search history.

(56) References Cited

U.S. PATENT DOCUMENTS

| 5,751,788 | A | 5/1998 | Khutoryansky et al. |
| 6,282,264 | B1 | 8/2001 | Smith et al. |
| 6,452,150 | B1 | 9/2002 | Mori et al. |
| 6,821,017 | B1 | 11/2004 | Tankersley |
| 7,014,362 | B2 * | 3/2006 | Beimier et al. ............... 378/206 |
| 7,046,764 | B1 | 5/2006 | Kump |
| 7,127,032 | B1 | 10/2006 | Kump |
| 2003/0194056 | A1 * | 10/2003 | Spahn ........................... 378/205 |

(Continued)

FOREIGN PATENT DOCUMENTS

JP 2000-105297 A 4/2000

(Continued)

OTHER PUBLICATIONS

Office Action, dated Sep. 22, 2009, issued in related U.S. Appl. No. 12/219,807, 9 pages.

(Continued)

*Primary Examiner* — Hoon Song
(74) *Attorney, Agent, or Firm* — Sughrue Mion, PLLC

(57) ABSTRACT

A radiation image capturing system detects the position of a radiation detecting cassette disposed below a patient and the position of a radiation source for emitting a radiation, based on the differences between the propagation times of radio waves emitted from an antenna device to an image capturing apparatus and the radiation detecting cassette. Based on the detected positions, the relative positions of the image capturing apparatus and the radiation detecting cassette are calculated, and then compared with each other by a position determining unit to judge how the image capturing apparatus is positioned with respect to the radiation detecting cassette. If the image capturing apparatus is not positioned in head-on facing relation to the radiation detecting cassette, then a warning is issued, and an actuating mechanism moves the image capturing apparatus to an appropriate position.

11 Claims, 23 Drawing Sheets

U.S. PATENT DOCUMENTS

| | | |
|---|---|---|
| 2005/0058244 A1 * | 3/2005 | Tanaka et al. .................. 378/62 |
| 2005/0069091 A1 | 3/2005 | Arakawa |
| 2006/0109958 A1 | 5/2006 | Ertel et al. |
| 2006/0261296 A1 | 11/2006 | Heath et al. |
| 2007/0023667 A1 | 2/2007 | Watanabe |
| 2009/0032744 A1 | 2/2009 | Kito et al. |

FOREIGN PATENT DOCUMENTS

| | | |
|---|---|---|
| JP | 2003-172783 A | 6/2003 |
| JP | 3494683 | 11/2003 |
| JP | 2006-305105 A | 11/2006 |
| JP | 2007-020679 A | 2/2007 |
| JP | 2007-037837 A | 2/2007 |

OTHER PUBLICATIONS

EP Communication, dated Jul. 6, 2010, issued in corresponding EP Application No. 08013372.1, 6 pages.

* cited by examiner

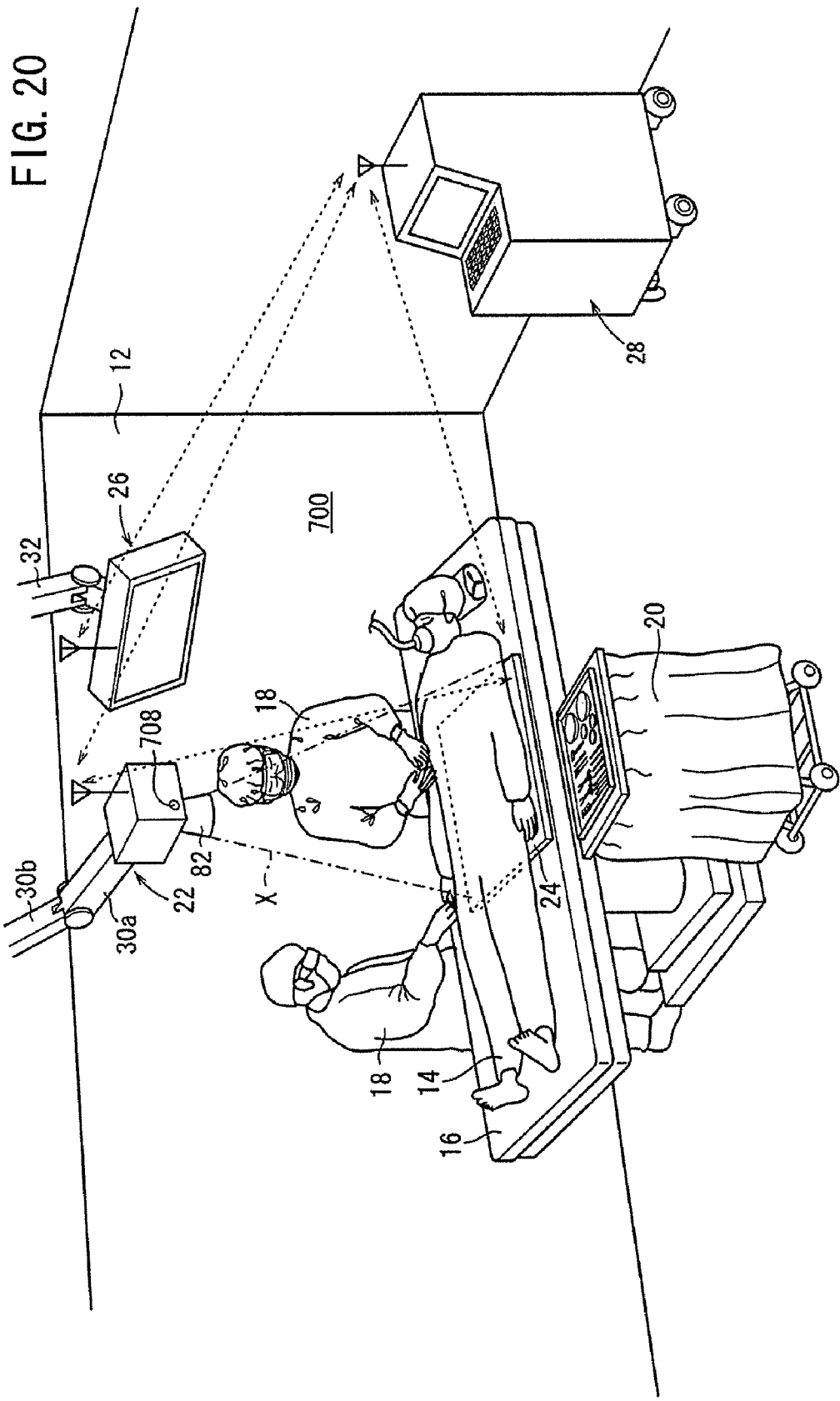

RADIATION IMAGE CAPTURING SYSTEM

This is a Continuation-In-Part of Application No. 12/179,740 filed Jul. 25, 2008. The entire disclosure of the prior application, application number 12/179,740, is hereby incorporated by reference.

BACKGROUND OF THE INVENTION

1. Field of the Invention

The present invention relates to a radiation image capturing system having a radiation conversion panel for converting a radiation that has passed through a subject into radiation image information.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. In such a radiation conversion panel, the radiation film with the recorded radiation image is supplied to a developing device to develop the image, or the stimulable phosphor panel is supplied to a reading device to obtain the radiation image as a visible image.

In the operating room or the like, it is necessary to read out and display a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read out a detected radiation image.

Such a radiation image capturing system is disclosed in Japanese Laid-Open Patent Publication No. 2007-037837, for example. In the disclosed radiation image capturing system, a radiation source for radiating X-rays is disposed above a subject lying on a lying table, and an X-ray image receiver is disposed below an affected part of the subject. X-rays emitted from the radiation source pass through the affected part of the subject, and detected by the X-ray image receiver, which converts the X-rays into an electric image signal.

In the radiation image capturing system, the X-ray image receiver has an image capturing surface which needs to be disposed in facing relation to the radiation source and the subject that are positioned upwardly of the X-ray image receiver. However, when the X-ray image receiver is positioned in alignment with the affected part of the subject, the X-ray image receiver may not be properly positioned in head-on alignment with the radiation source. If an image capturing cycle is carried out while the X-ray image receiver is not facing the radiation source head-on, then the X-ray image receiver is unable to capture a radiation image of the affected part of the subject. Therefore, it is necessary to reset the X-ray image receiver in a desired position and then to perform an image capturing cycle. As a result, the efficiency of the process of capturing a radiation image of the affected part of the subject is relatively low.

SUMMARY OF THE INVENTION

It is a general object of the present invention to provide a radiation image capturing system which allows a radiation conversion panel to be reliably and accurately placed in a desired position that faces a radiation source head-on, for thereby efficiently capturing a radiation image of a subject.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 20 is a perspective view inside an operating room incorporating a radiation image capturing system according to a third embodiment of the present invention;

DESCRIPTION OF THE PREFERRED EMBODIMENTS

Figure 1:
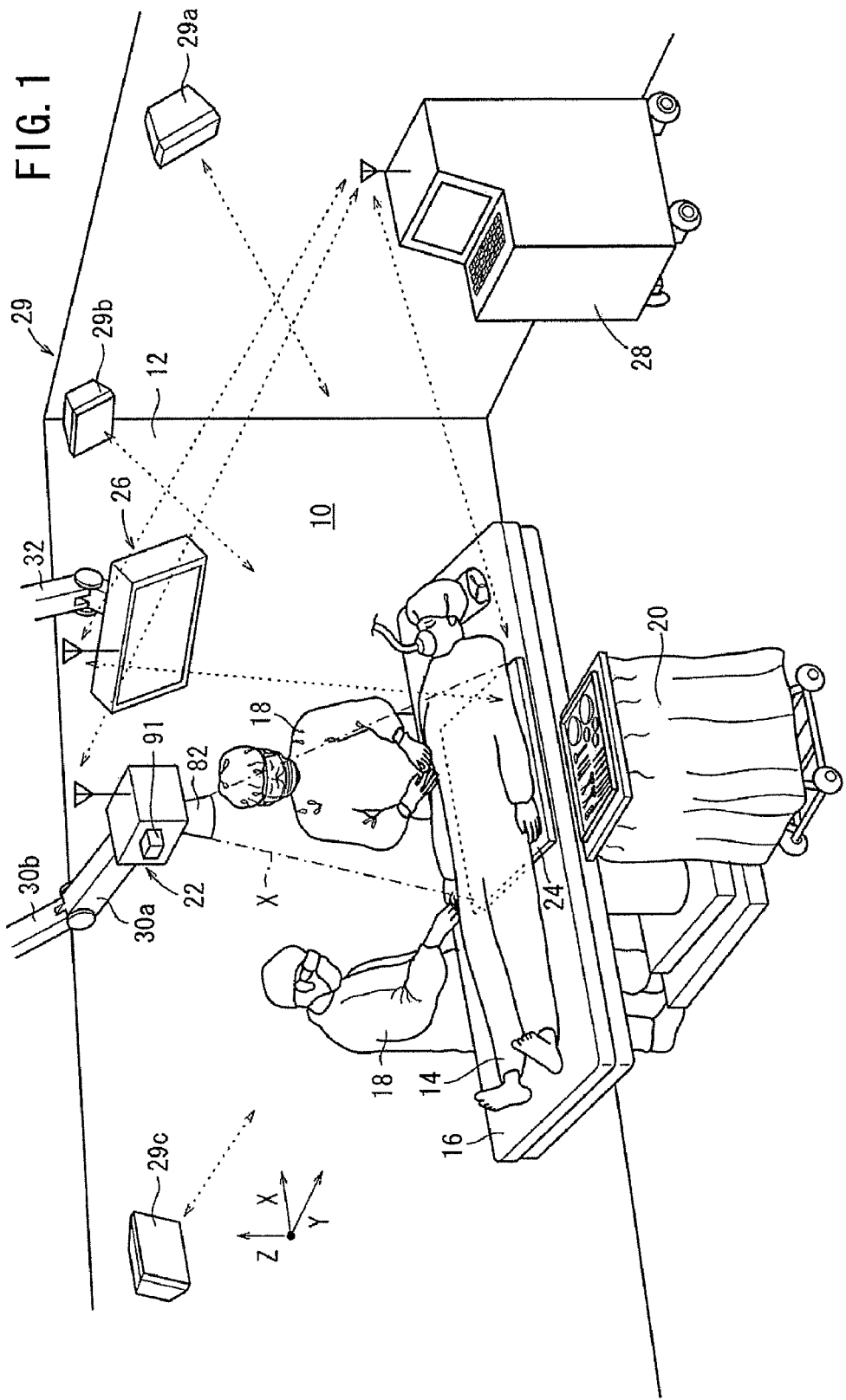
FIG. 1 is a perspective view inside an operating room incorporating a radiation image capturing system according to a first embodiment of the present invention.
Figure 2:
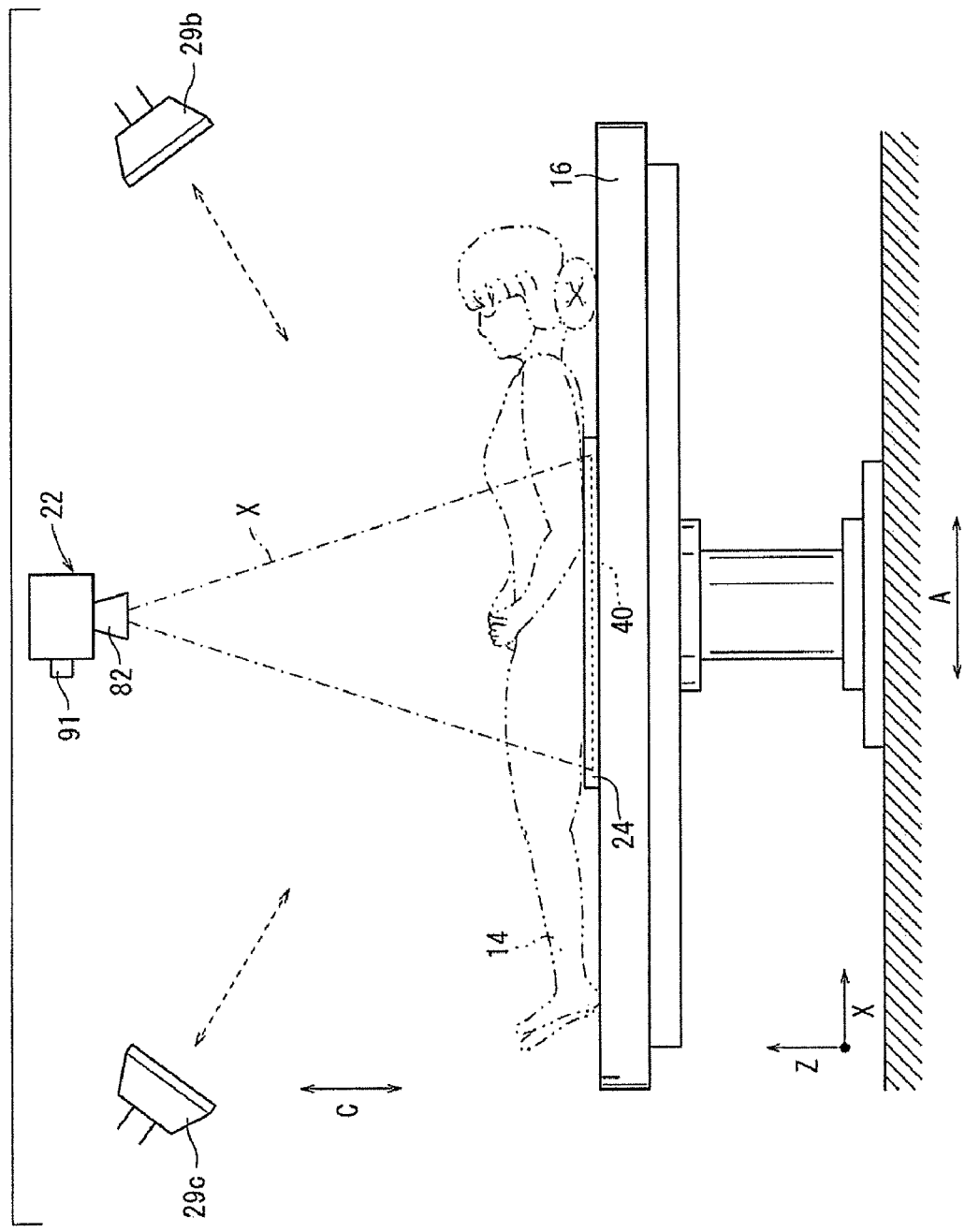
FIG. 2 is a side elevational view of a surgical table with a patient lying thereon in the operating room shown in FIG. 1.
Figure 3:
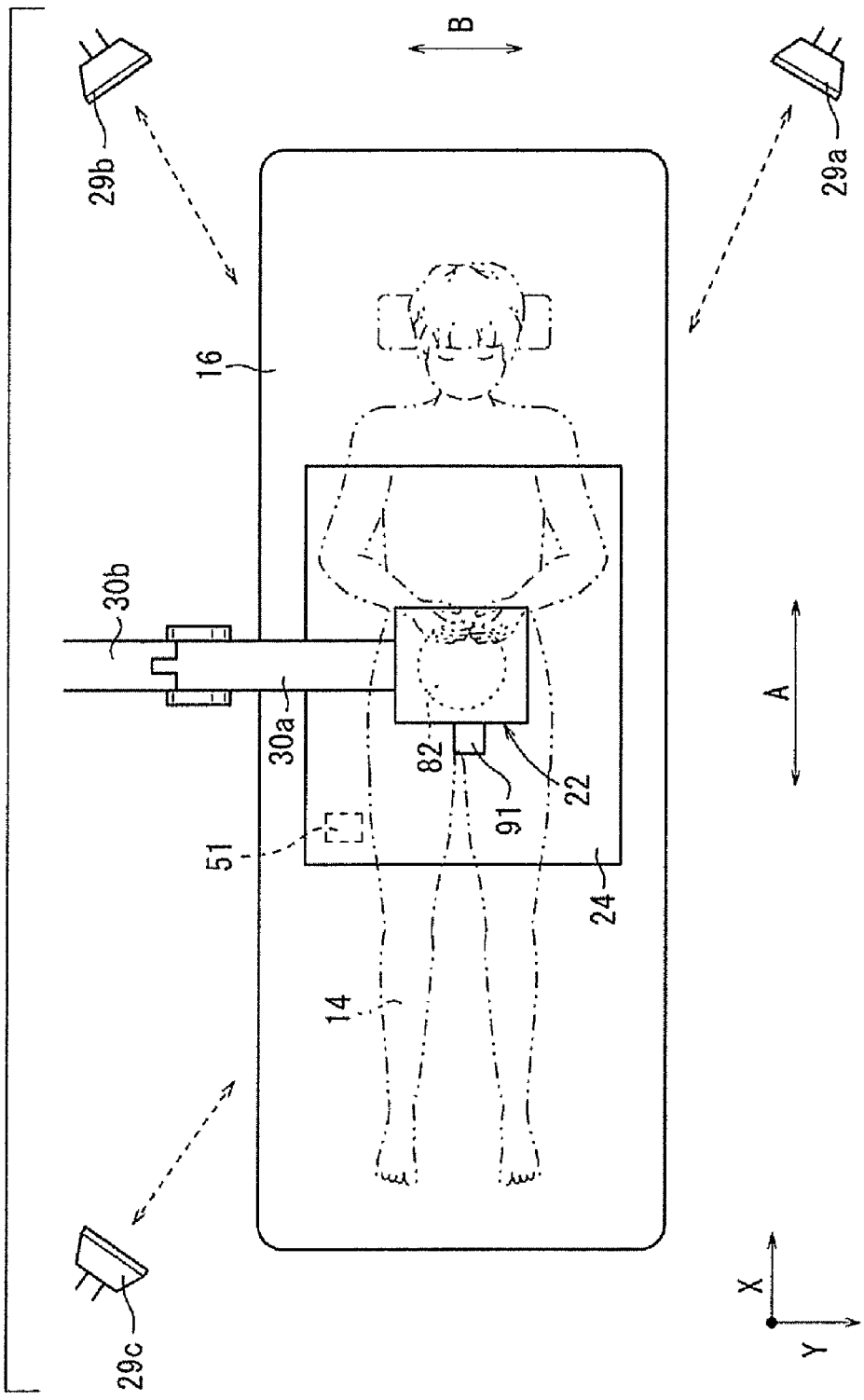
FIG. 3 is a plan view of the surgical table with the patient lying thereon in the operating room shown in FIG. 1.

FIGS. 1 through 3 show an operating room 12 incorporating a radiation image capturing system 10 according to a first embodiment of the present invention. As shown in FIG. 1, the operating room 12 has, in addition to the radiation image capturing system 10, a surgical table 16 for a patient 14 to lie thereon, and an instrument table 20 disposed to one side of the surgical table 16 for placing thereon various tools and instruments to be used by surgeons 18 for operating the patient 14. The surgical table 16 is surrounded by various apparatus required for surgical operations, including an anesthesia apparatus, an aspirator, an electrocardiograph, a blood pressure monitor, etc.

The radiation image capturing system 10 includes an image capturing apparatus (image capturing unit) 22 for irradiating the patient 14 with a radiation X at a dosage according to image capturing conditions, a radiation detecting cassette 24 housing therein a radiation detector (radiation conversion panel) 40, to be described later, for detecting the radiation X that has passed through the patient 14, a display device 26 for displaying a radiation image based on the radiation X that is detected by the radiation detector 40, and a console 28 for controlling the image capturing apparatus 22, the radiation detecting cassette 24, and the display device 26. The image capturing apparatus 22, the radiation detecting cassette 24, the display device 26, and the console 28 transmit and receive signals by way of wireless communications.

The operating room 12 also has an antenna device (position detecting unit) 29 for detecting three-dimensional positions of the image capturing apparatus 22 and the radiation detecting cassette 24. The antenna device 29 comprises first, second, and third transceivers 29a, 29b, 29c each positioned in any one of the four corners of the operating room 12, for example, and connected to the console 28. The first, second, and third transceivers 29a, 29b, 29c are capable of transmitting radio waves to the image capturing apparatus 22 and the radiation detecting cassette 24, and of receiving radio waves from first and second receivers 51, 91 (see FIG. 3) disposed respectively in the image capturing apparatus 22 and the radiation detecting cassette 24.

The image capturing apparatus 22 is coupled to a plurality of universal arms 30a, 30b so as to be movable to a desired position for capturing an image at a desired area of the patient 14 and also to be retractable to a position out of the way while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 4:
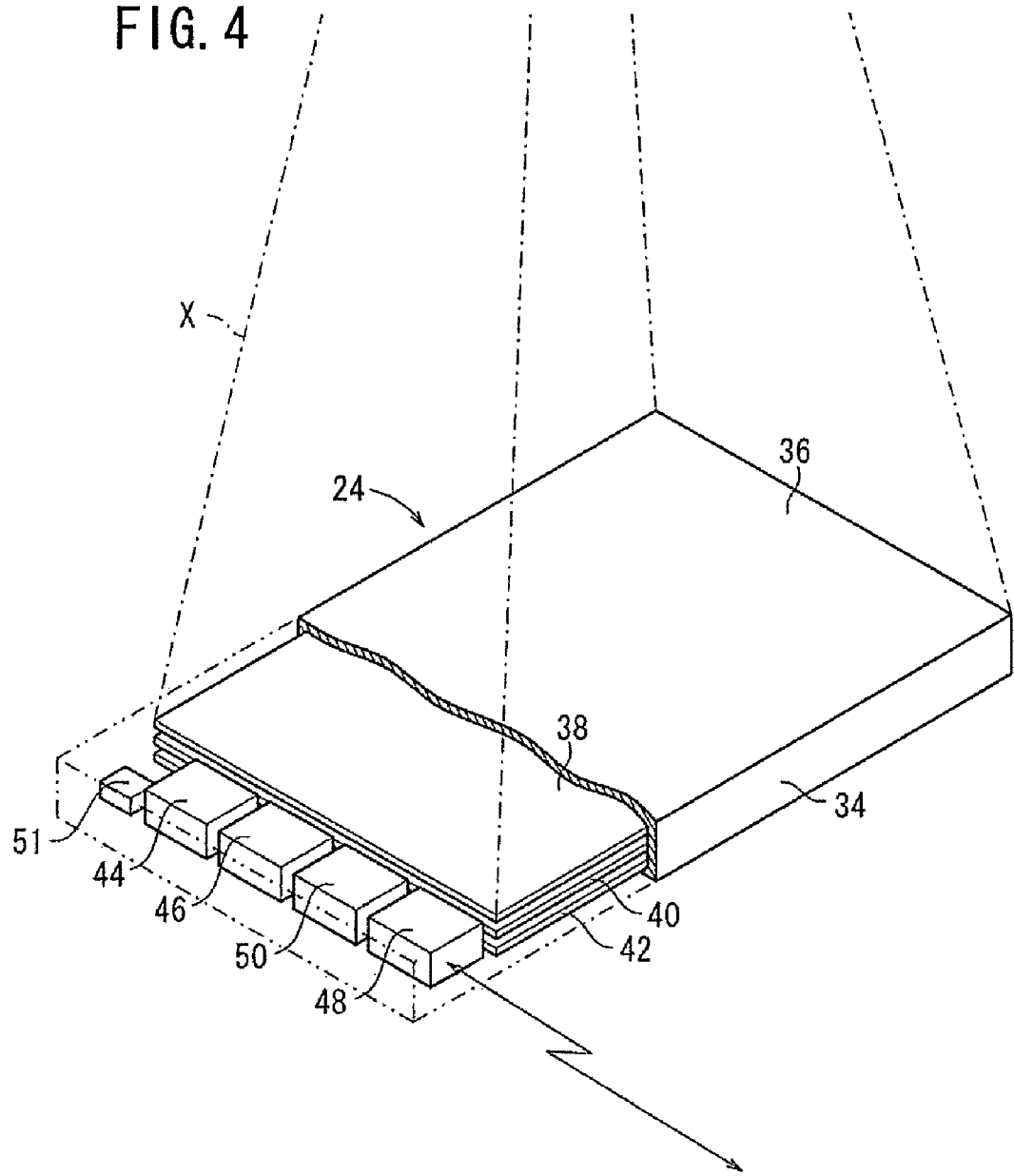
FIG. 4 is a perspective view, partly cut away, showing internal structural details of a radiation detecting cassette used in the radiation image capturing system.

FIG. 4 shows internal structural details of the radiation detecting cassette 24. As shown in FIG. 4, the radiation detecting cassette 24 has a casing 34 made of a material permeable to the radiation X. The casing 34 houses therein a grid 38 for removing scattered rays of the radiation X from the patient 14, a radiation detector 40 for detecting the radiation X that has passed through the patient 14, and a lead plate 42 for absorbing back scattered rays from the radiation X. The grid 38, the radiation detector 40 and the lead plate 42 are successively arranged in that order from a surface 36 of the casing 34 which is irradiated with the radiation X. The irradiated surface 36 of the casing 34 may be constructed as the grid 38.

The casing 34 also houses therein a battery 44 as a power supply of the radiation detecting cassette 24, a cassette controller 46 for energizing the radiation detector 40 with electric power supplied from the battery 44, a transceiver 48 for sending and receiving signals including the information of the radiation X detected by the radiation detector 40, to and from the console 28, a first detector 50 for detecting the direction, tilt, etc. of the radiation detecting cassette 24, and a first receiver (position detecting unit) 51 for receiving radio waves transmitted from the antenna device 29.

Figure 6:
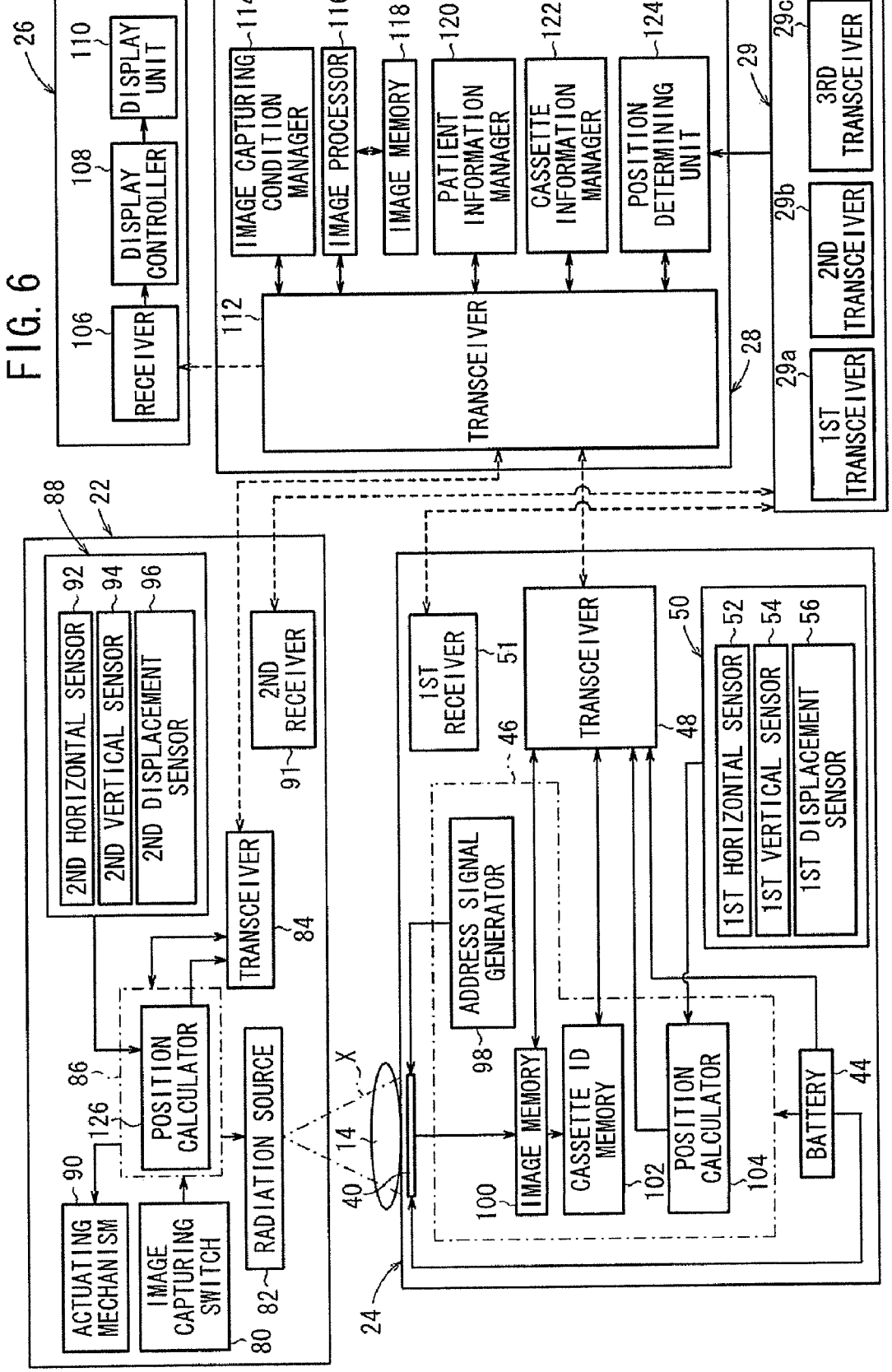
FIG. 6 is a block diagram of the radiation image capturing system.

As shown in FIG. 6, the first detector 50 comprises a first horizontal sensor 52 for detecting a horizontal position (in the directions indicated by the arrows A, B in FIG. 3) of the radiation detecting cassette 24 in the operating room 12, a first vertical sensor 54 for detecting a vertical position (in the directions indicated by the arrow C in FIG. 2) of the radiation detecting cassette 24 in the operating room 12, and a first displacement sensor 56 for detecting a displacement of the radiation detecting cassette 24.

The first horizontal sensor 52 comprises an azimuthal sensor for detecting a horizontal position in space based on geomagnetism, for example. The first vertical sensor 54 comprises a gravitational sensor. The first displacement sensor 56 comprises an acceleration sensor for detecting an acceleration generated when the radiation detecting cassette 24 is displaced.

As shown in FIG. 6, the first horizontal sensor 52, the first vertical sensor 54, and the first displacement sensor 56 of the first detector 50 output detected signals indicative of detected quantities to the cassette controller 46. The cassette controller 46 includes a position calculator 104, described later, which calculates the direction, tilt, etc. of the radiation detecting cassette 24 based on the detected signals.

The first horizontal sensor 52, the first vertical sensor 54, and the first displacement sensor 56, which have different characteristics, are thus combined to detect various quantities of the radiation detecting cassette 24, from which the direction, tilt, etc. of the radiation detecting cassette 24 can be detected accurately.

A shield plate of lead or the like such as the lead plate 42 should preferably be placed over the side surfaces of the cassette controller 46, the transceiver 48, the first detector 50, and the first receiver 51 under the irradiated surface 36 of the casing 34 to protect the cassette controller 46, the transceiver 48, the first detector 50, and the first receiver 51 against damage which would otherwise be caused if those were irradiated with the radiation X.

Figure 5:
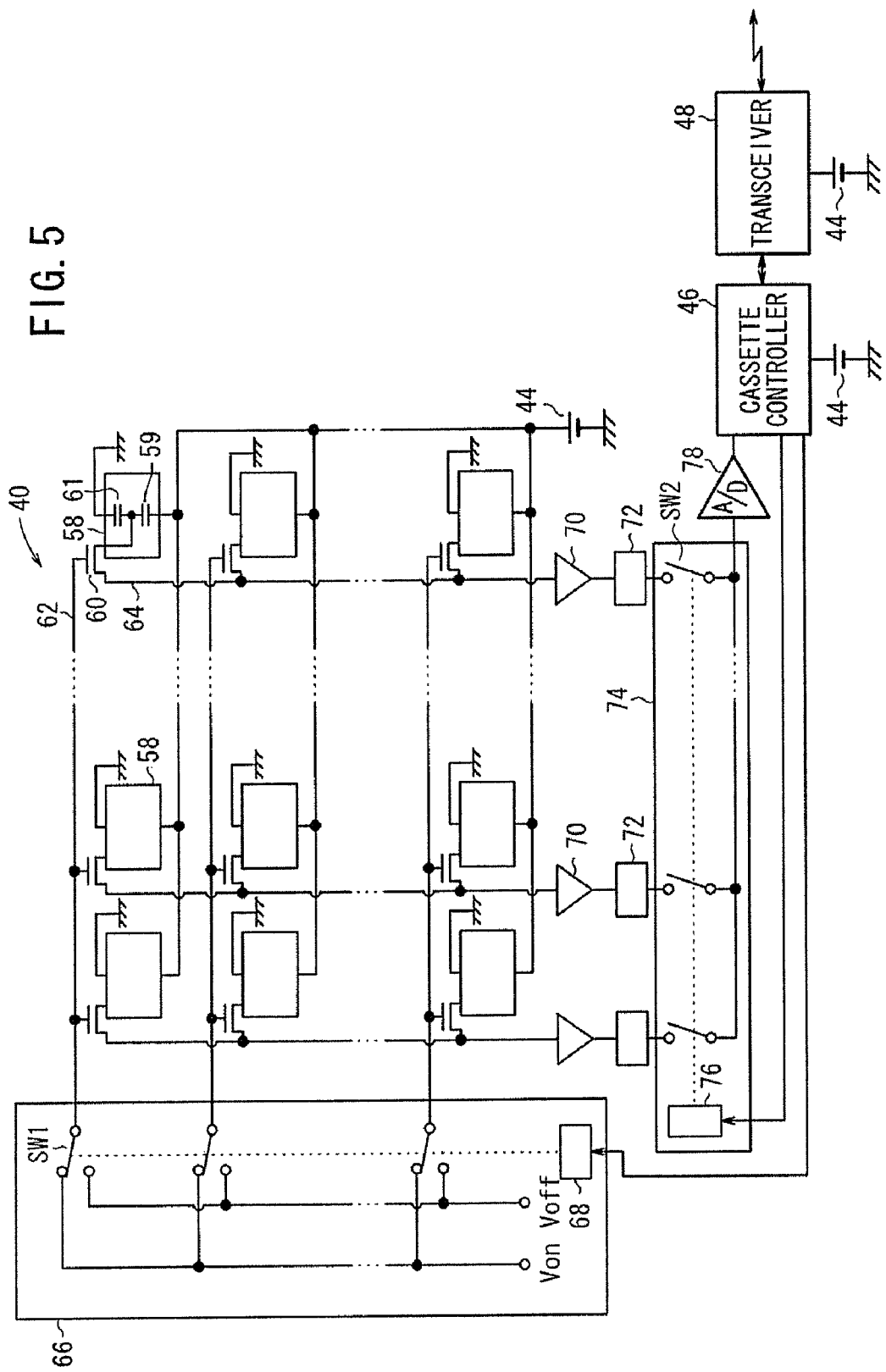
FIG. 5 is a block diagram of a circuit arrangement of a radiation detector.

FIG. 5 shows in block form a circuit arrangement of the radiation detector 40. As shown in FIG. 5, the radiation detector 40 comprises an array of thin-film transistors (TFTs) 60 arranged in rows and columns, a photoelectric conversion layer 59 made of a material such as amorphous selenium (a-Se) for generating electric charges upon detection of the radiation X, the photoelectric conversion layer 59 being disposed over the array of TFTs 60, and an array of storage capacitors 61 connected to the photoelectric conversion layer 59. When the radiation X is applied to the radiation detector 40, the photoelectric conversion layer 59 generates electric charges, and the storage capacitors 61 store the generated electric charges. Then, the TFTs 60 are turned on along each row at a time to read out the electric charges from the storage capacitors 61 as an image signal. In FIG. 5, the photoelectric conversion layer 59 and one of the storage capacitors 61 are shown as a pixel 58, and the pixel 58 is connected to one of the TFTs 60. Details of the other pixels 58 are omitted from illustration.

Since amorphous selenium tends to change its structure and lose its functionality at high temperatures, amorphous selenium needs to be used within a certain temperature range. Therefore, some means for cooling the radiation detector 40 should preferably be provided in the radiation detecting cassette 24.

The TFTs 60 connected to the respective pixels 58 are connected to respective gate lines 62 extending parallel to the rows and respective signal lines 64 extending parallel to the columns. The gate lines 62 are connected to a line scanning driver 66, and the signal lines 64 are connected to a multiplexer 74 serving as a reading circuit.

The gate lines 62 are supplied with control signals Von, Voff from the line scanning driver 66 for turning on and off the TFTs 60 along the rows. The line scanning driver 66 comprises a plurality of switches SW1 for switching between the gate lines 62 and an address decoder 68 for outputting a selection signal for selecting one of the switches SW1 at a time. The address decoder 68 is supplied with an address signal from the cassette controller 46.

The signal lines 64 are supplied with electric charges stored in the storage capacitors 61 of the pixels 58 through the TFTs 60 arranged in the columns. The electric charges supplied to the signal lines 64 are amplified by amplifiers 70 connected respectively to the signal lines 64. The amplifiers 70 are connected through respective sample and hold circuits 72 to the multiplexer 74. The multiplexer 74 comprises a plurality of switches SW2 for successively switching between the signal lines 64 and an address decoder 76 for outputting a selection signal for selecting one of the switches SW2 at a time. The address decoder 76 is supplied with an address signal from the cassette controller 46. The multiplexer 74 has an output terminal connected to an A/D converter 78. A radiation image signal generated by the multiplexer 74 based on the electric charges from the sample and hold circuits 72 is converted by the A/D converter 78 into a digital image signal representing radiation image information, which is supplied to the cassette controller 46.

The TFTs 60 functioning as a switching device can be combined with another image capturing device such as a CMOS (Complementary Metal Oxide Semiconductor) device. Further, the TFTs 60 may be replaced by a CCD (Charge Coupled Device) which transfers charge while shifting the charge with the shift pulse corresponding to the gate signal for the TFTs.

FIG. 6 shows in block form the radiation image capturing system 10 which comprises the image capturing apparatus 22, the radiation detecting cassette 24, the display device 26, and the console 28.

The image capturing apparatus 22 comprises an image capturing switch 80, a radiation source 82 for outputting the radiation X, a transceiver 84 for receiving image capturing conditions from the console 28 by way of wireless communications and transmitting an image capturing completion signal, etc. to the console 28 by way of wireless communications, a radiation source controller 86 for controlling the radiation source 82 based on an image capturing start signal supplied from the image capturing switch 80 and image capturing conditions supplied from the transceiver 84, a second detector 88 for detecting the position of the image capturing apparatus 22, and an actuating mechanism (actuating unit) 90 for moving the image capturing apparatus 22 to a desired position based on the position detected by the second detector 88. A second receiver (position detecting unit) 91 for receiving radio waves transmitted from the antenna device 29 is mounted on a side wall of the image capturing apparatus 22.

The second detector 88 comprises a second horizontal sensor 92 for detecting a horizontal position (in the directions indicated by the arrows A, B in FIG. 3) of the image capturing apparatus 22 in the operating room 12, a second vertical sensor 94 for detecting a vertical position (in the directions indicated by the arrow C in FIG. 2) of the image capturing apparatus 22 in the operating room 12, and a second displacement sensor 96 for detecting a displacement of the image capturing apparatus 22, for example, as with the first detector 50 shown above.

The second horizontal sensor 92 comprises an azimuthal sensor for detecting a horizontal position in space based on geomagnetism, for example. The second vertical sensor 94 comprises a gravitational sensor. The second displacement sensor 96 comprises an acceleration sensor for detecting an acceleration generated when the image capturing apparatus 22 is displaced.

The second horizontal sensor 92, the second vertical sensor 94, and the second displacement sensor 96 of the second detector 88 output detected signals indicative of detected quantities to the radiation source controller 86. The radiation source controller 86 includes a position calculator 126, described later, which calculates the direction, tilt, etc. of the image capturing apparatus 22 based on the supplied detected signals.

The second horizontal sensor 92, the second vertical sensor 94, and the second displacement sensor 96, which have different characteristics, are thus combined to detect various quantities of the image capturing apparatus 22, from which the direction, tilt, etc. of the image capturing apparatus 22 can be detected by the position calculator 126.

The actuating mechanism 90 comprises stepping motors, actuators, or the like which are disposed in junctions of the universal arms 30a, 30b for tilting the universal arms 30a, 30b relatively to each other for universally moving the image capturing apparatus 22. The actuating mechanism 90 is electrically connected to the radiation source controller 86, and can be energized by a control signal output from the radiation source controller 86 to move the image capturing apparatus 22 to a desired position.

The radiation detecting cassette 24 houses therein the radiation detector 40, the battery 44, the cassette controller 46, the transceiver 48, the first detector 50, and the first receiver 51.

The cassette controller 46 comprises an address signal generator 98 for supplying address signals to the address decoder 68 of the line scanning driver 66 and the address decoder 76 of the multiplexer 74 of the radiation detector 40, an image memory 100 for storing the radiation image information detected by the radiation detector 40, a cassette ID memory 102 for storing cassette ID information for identifying the radiation detecting cassette 24, and the position calculator 104 for calculating the position of the radiation detecting cassette 24 in the operating room 12 based on the detected quantities from the first detector 50.

The transceiver 48 receives a transmission request signal from the console 28 by way of wireless communications and transmits the cassette ID information stored in the cassette ID memory 102, the radiation image information stored in the image memory 100, and the information representing the direction, tilt, etc. of the radiation detecting cassette 24 detected by the first detector 50, to the console 28 by way of wireless communications.

The display device 26 comprises a receiver 106 for receiving radiation image information from the console 28, a display controller 108 for controlling the display of the received radiation image information, and a display unit (warning unit) 110 for displaying the radiation image information processed by the display controller 108.

The console 28 comprises a transceiver 112 for transmitting and receiving necessary information including radiation image information, positional information, etc. to and from the image capturing apparatus 22, the radiation detecting cassette 24, and the display device 26 by way of wireless communications, an image capturing condition manager 114 for managing image capturing conditions required for the image capturing apparatus 22 to capture radiation images, an image processor 116 for processing radiation image information transmitted from the radiation detecting cassette 24, an image memory 118 for storing the radiation image information processed by the image processor 116, a patient information manager 120 for managing patient information of the patient 14 whose images are to be captured, a cassette information manager 122 for managing cassette information transmitted from the radiation detecting cassette 24, and a position determining unit 124 for determining the relative positional relationship between the image capturing apparatus 22 and the radiation detecting cassette 24 based on the propagation times "t" of radio waves that are transmitted from the antenna device 29 to the image capturing apparatus 22 and the radiation detecting cassette 24.

The console 28 may be located outside of the operating room 12 insofar as it can transmit and receive signals to and from the image capturing apparatus 22, the radiation detecting cassette 24, and the display device 26 by way of wireless communications.

The position determining unit 124 is supplied, through the transceivers 48, 84, 112, with positional information of the image capturing apparatus 22 and the radiation detecting cassette 24 which is detected based on the differences between the propagation times "t" of radio waves detected by the antenna device 29 which includes the first, second, and third transceivers 29a, 29b, 29c, and compares the relative positions of the image capturing apparatus 22 and the radiation detecting cassette 24 with each other.

The position determining unit 124 determines whether or not the radiation detecting cassette 24 and the image capturing apparatus 22 are positioned in vertically head-on facing relation to each other. If the radiation detecting cassette 24 and the image capturing apparatus 22 are not positioned in vertically head-on facing relation to each other, i.e., if they are not vertically aligned with each other, then the position determining unit 124 outputs a control signal through the transceiver 112 to the radiation source controller 86, which energizes the actuating mechanism 90.

Therefore, the position determining unit 124 functions as a determining means for determining whether or not the radiation detecting cassette 24 and the image capturing apparatus 22 are positioned in vertically head-on facing relation to each other. The positional information of the image capturing apparatus 22 and the radiation detecting cassette 24 is expressed as XYZ coordinates, for example.

When the radiation detecting cassette 24 and the image capturing apparatus 22 are positioned in vertically head-on facing relation to each other, the radiation detecting cassette 24 is positioned directly below (vertically downwardly of) the image capturing apparatus 22 as it is viewed from above (see FIG. 3). Stated otherwise, if it is assumed that the surgical table 16 has its longitudinal direction extending along an X-axis, its transverse direction extending along a Y-axis, and its vertical direction extending along a Z-axis, then the center of the radiation detecting cassette 24 and the radiation source 82 at the center of the image capturing apparatus 22 are aligned with each other in an XY plane defined by the X-axis and the Y-axis, and are spaced from each other by a certain distance only in the vertical direction (indicated by the arrow C) along the Z-axis (see FIG. 2).

The radiation image capturing system 10 according to the first embodiment is basically constructed as described above, and operation of the radiation image capturing system 10 will be described below.

The radiation image capturing system 10 is installed in the operating room 12 and used when a radiation image of the patient 14 is required by the surgeons 18 who are performing an operation on the patient 14. Before a radiation image of the patient 14 is captured, patient information of the patient 14 to be imaged is registered in the patient information manager 120 of the console 28. If an area of the patient 14 to be imaged and an image capturing method have already been known, they are registered as image capturing conditions in the image capturing condition manager 114. After the above preparatory process is finished, the surgeons 18 perform an operation on the patient 14.

For capturing a radiation image of the patient 14 during the operation, one of the surgeons 18 or the radiological technician places the radiation detecting cassette 24 in a given position between the patient 14 and the surgical table 16 with the irradiated surface 36 facing the image capturing apparatus 22.

At this time, the first, second, and third transceivers 29a, 29b, 29c of the antenna device 29 emit radio waves, which are received by the first receiver 51 housed in the radiation detecting cassette 24 and the second receiver 91 mounted on the image capturing apparatus 22. The position determining unit 124 of the console 28 calculates the propagation times "t" of the radio waves emitted from the respective the first, second, and third transceivers 29a, 29b, 29c, from the time the radio waves are emitted until they are received by the first and second receivers 51, 91, and specifies the positions of the first and second receivers 51, 91 in the operating room 12 based on the differences between the propagation times "t". In other words, the position determining unit 124 calculates the relative positions of the radiation detecting cassette 24 having the first receiver 51 and the image capturing apparatus 22 having the second receiver 91.

Then, based on the positional relationship between the image capturing apparatus 22 and the radiation detecting cassette 24 in the operating room 12, the position determining unit 124 determines whether or not the image capturing apparatus 22 is positioned upwardly of the radiation detecting cassette 24 in vertically head-on facing relation thereto in the direction indicated by the arrow C. Stated otherwise, the position determining unit 124 determines whether the image capturing apparatus 22 has been moved to and disposed in a given position which faces the affected part of the patient 14 head-on.

If the position determining unit 124 judges that the image capturing apparatus 22 is positioned upwardly of the radiation detecting cassette 24 in vertically head-on facing relation thereto, then the first horizontal sensor 52, the first vertical sensor 54, and the first displacement sensor 56 of the first detector 50 detect the direction, tilt, etc. of the radiation detecting cassette 24. At the same time, the second horizontal sensor 92, the second vertical sensor 94, and the second displacement sensor 96 of the second detector 88 detect the direction, tilt, etc. of the image capturing apparatus 22. The first detector 50 outputs detected signals indicative of the detected quantities to the position calculator 104 of the cassette controller 46, and the second detector 88 outputs detected signals indicative of the detected quantities to the position calculator 126 of the radiation source controller 86. The position calculators 104, 126 then calculate the directions, tilts, etc. of the image capturing apparatus 22 and the radiation detecting cassette 24. The information representing the calculated directions, tilts, etc. is transmitted from the position calculators 104, 126 through the transceivers 48, 84 to the console 28. In the console 28, the transmitted information is supplied through the transceiver 112 to the position determining unit 124.

The position determining unit 124 now confirms that the image capturing apparatus 22 and the radiation detecting cassette 24 are facing each other head-on in one direction without being tilted with respect to each other.

After having confirmed that the image capturing apparatus 22 and the radiation detecting cassette 24 are facing each other head-on, one of the surgeons 18 or the radiological technician turns on the image capturing switch 80 to capture a radiation image of the patient 14. The radiation source controller 86 of the image capturing apparatus 22 acquires the image capturing conditions for the area of the patient 14 to be imaged from the image capturing condition manager 114 of the console 28 through the transceivers 84, 112 by way of wireless communications, and controls the radiation source 82 according to the acquired image capturing conditions to apply a radiation X at a given dosage to the patient 14.

Based on the positional information of the image capturing apparatus 22 and the radiation detecting cassette 24, if the position determining unit 124 judges that the image capturing apparatus 22 is not positioned upwardly of the radiation detecting cassette 24 in vertically head-on facing relation thereto, then it is determined that the radiation X from the image capturing apparatus 22 will not be applied to the affected area of the patient 14 and the radiation detector 40 of the radiation detecting cassette 24, and a desired radiation image of the affected area of the patient 14 will not be captured. Based on the determination, the position determining unit 124 gives the console 28, the display device 26, etc. a warning indicating that the image capturing apparatus 22 including the radiation source 82 and the radiation detecting cassette 24 are not placed in the desired position.

At the same time, the position determining unit 124 outputs a control signal through the transceivers 112, 84 to the radiation source controller 86, which outputs an actuating signal to the actuating mechanism 90. In response to the actuating signal, the actuating mechanism 90 turns the universal arms 30a, 30b through respective given angles to move the image capturing apparatus 22 on the end of the universal arm 30a to a position which faces the radiation detecting cassette 24 head-on.

The distance that the image capturing apparatus 22 is to travel at this time is determined based on the difference between the positional information of the radiation detecting cassette 24 and the positional information of the image capturing apparatus 22. The actuating signal output from the radiation source controller 86 to the actuating mechanism 90 is based on the difference between the positional information of the radiation detecting cassette 24 and the positional information of the image capturing apparatus 22.

After the image capturing apparatus 22 has moved the given distance, the relative positional relationship between the image capturing apparatus 22 and the radiation detecting cassette 24 is confirmed again based on radio waves emitted from the antenna device 29 and received by the first and second receivers 51, 91. After having confirmed again that the image capturing apparatus 22 and the radiation detecting cassette 24 are facing each other head-on, one of the surgeons 18 or the radiological technician turns on the image capturing switch 80 to capture a radiation image of the patient 14. At this time, the first and second detectors 50, 88 also detect the directions, tilts, etc. of the radiation detecting cassette 24 and the image capturing apparatus 22 for the position determining unit 124 to confirm that the image capturing apparatus 22 and the radiation detecting cassette 24 are facing each other head-on in one direction without being tilted with respect to each other.

The radiation X which has been applied from the radiation source 82 to the patient 14 and has passed through the patient 14 is applied to the grid 38 of the radiation detecting cassette 24, which removes scattered rays of the radiation X. Then, the radiation X is applied to the radiation detector 40, and converted into electric signals by the photoelectric conversion layer 59 of the pixels 58 of the radiation detector 40. The electric signals are stored as electric charges in the storage capacitors 61 (see FIG. 5). The stored electric charges in the storage capacitors 61, which represent radiation image information of the patient 14, are read out from the storage capacitors 61 according to address signals which are supplied from the address signal generator 98 of the cassette controller 46 to the line scanning driver 66 and the multiplexer 74.

Specifically, in response to the address signal supplied from the address signal generator 98, the address decoder 68 of the line scanning driver 66 outputs a selection signal to select one of the switches SW1, which supplies the control signal Von to the gates of the TFTs 60 connected to the gate line 62 corresponding to the selected switch SW1. In response to the address signal supplied from the address signal generator 98, the address decoder 76 of the multiplexer 74 outputs a selection signal to successively turn on the switches SW2 to switch between the signal lines 64 for thereby reading out the electric charges stored in the storage capacitors 61 of the pixels 58 connected to the selected gate line 62 that is selected by the line scanning driver 66, through the signal lines 64.

The electric charges read out from the storage capacitors 61 of the pixels 58 connected to the selected gate line 62 are amplified by the respective amplifiers 70, sampled by the sample and hold circuits 72, and supplied to the multiplexer 74. Based on the supplied electric charges, the multiplexer 74 generates and supplies a radiation image signal to the A/D converter 78, which converts the radiation image signal into a digital signal. The digital signal which represents the radiation image information is stored in the image memory 100 of the cassette controller 46, and thereafter transmitted from the transceiver 48 to the console 28 by way of wireless communications.

Similarly, the address decoder 68 of the line scanning driver 66 successively turns on the switches SW1 to switch between the gate lines 62 according to the address signal supplied from the address signal generator 98. The electric charges stored in the storage capacitors 61 of the pixels 58 connected to the successively selected gate lines 62 are read out through the signal lines 64, and processed by the multiplexer 74 and the A/D converter 78 into digital signals, which are stored in the image memory 100 of the cassette controller 46.

The radiation image information transmitted to the console 28 is received by the transceiver 112, processed by the image processor 116, and then stored in the image memory 118 in association with the patient information of the patient 14 registered in the patient information manager 120.

The radiation image information processed by the image processor 116 is transmitted from the transceiver 112 to the display device 26. In the display device 26, the receiver 106 receives the radiation image information, and the display controller 108 controls the display unit 110 to display a radiation image based on the radiation image information. The surgeons 18 perform a surgical operation on the patient 14 while watching the radiation image displayed on the display unit 110.

Since no cables for transmitting and receiving signals are connected between the radiation detecting cassette 24 and the console 28, between the image capturing apparatus 22 and the console 28, and between the console 28 and the display device 26, it is not necessary to lay such cables on the floor of the operating room 12 and hence there are no cable-induced obstacles to the operation performed by the surgeons 18, the radiological technician, or other staff members in the operating room 12.

In the above embodiment, the first and second displacement sensors 56, 96 of the first and second detectors 50, 88 comprise acceleration sensors as described above. However, the first and second displacement sensors 56, 96 may comprise gyro sensors. If the first and second displacement sensors 56, 96 comprise gyro sensors, then they can detect angular displacements of the image capturing apparatus 22 and the radiation detecting cassette 24, and the detected angular displacements may be combined with the detected signals from the first and second horizontal sensors 52, 92 and the first and second vertical sensors 54, 94 to detect directions, tilts, etc. of the image capturing apparatus 22 and the radiation detecting cassette 24.

In the first embodiment, furthermore, the antenna device 29 comprising the first, second, and third transceivers 29a, 29b, 29c is disposed in the operating room 12, and the first and second receivers 51, 91 are combined with the image capturing apparatus 22 and the radiation detecting cassette 24, respectively, for specifying the positions of the image capturing apparatus 22 and the radiation detecting cassette 24. However, the present invention is not limited to such a configuration. Base stations for transmitting and receiving UWB (Ultra Wide Band) signals may be combined with the image capturing apparatus 22 and the console 28, respectively, and a UWB receiver such as a tag, for example, for receiving such UWB signals may be housed in the radiation detecting cassette 24. According to such a modification, the propagation times of UWB signals from the UWB receiver to the base stations may be calculated, and the position of the radiation detecting cassette 24 with the UWB receiver may be specified based on the difference between the calculated propagation times.

If the transceiver 48 in the radiation detecting cassette 24 comprises a transceiver capable of UWB communications, then the radiation detecting cassette 24 needs no separate UWB receiver, but the transceiver 48 can also be used to transmit and receive UWB signals.

According to the first embodiment, as described above, the position of the image capturing apparatus 22 including the radiation source 82 and the position of the radiation detecting cassette 24 housing the radiation detector 40 are detected by the antenna device 29 and the first and second receivers 51, 91 which serve as the position detecting unit. Based on the detected positional information, the position determining unit 124 of the console 28 determines whether or not the image capturing apparatus 22 and the radiation detecting cassette 24 face each other head-on. Consequently, it is possible to recognize in advance when the image capturing apparatus 22 does not face the radiation detecting cassette 24 head-on and cannot capture a radiation image of the patient 14 properly.

If the image capturing apparatus 22 does not face the radiation detecting cassette 24 head-on and cannot capture a radiation image of the patient 14 properly, then the actuating mechanism 90 of the image capturing apparatus 22 can move the image capturing apparatus 22 to a position which faces the radiation detecting cassette 24 head-on. Therefore, the image capturing apparatus 22 and the radiation detecting cassette 24 can reliably and accurately be placed in respective positions for capturing a radiation image. In addition, as wrong radiation images are prevented from being captured when the image capturing apparatus 22 and the radiation detecting cassette 24 are not properly positioned relatively to each other, proper radiation images can be captured highly efficiently.

When the radiation image capturing system 10 is in actual use, the position determining unit 124 may determine whether or not the radiation detecting cassette 24 and the image capturing apparatus 22 face each other head-on according to a rough criterion. In such a case, an optimum criterion may be used for the position determining unit 124 to determine whether or not the radiation detecting cassette 24 and the image capturing apparatus 22 face each other head-on.

Another example of the first embodiment will be described below with reference to FIGS. 7 through 9. According to the other example, the surgical table 16 in the operating room 12 incorporating the radiation image capturing system 10 shown in FIG. 1 is replaced with a stretcher 150 (see FIG. 7) that can be moved into the operating room 12 with the patient 14 lying thereon.

Figure 7:
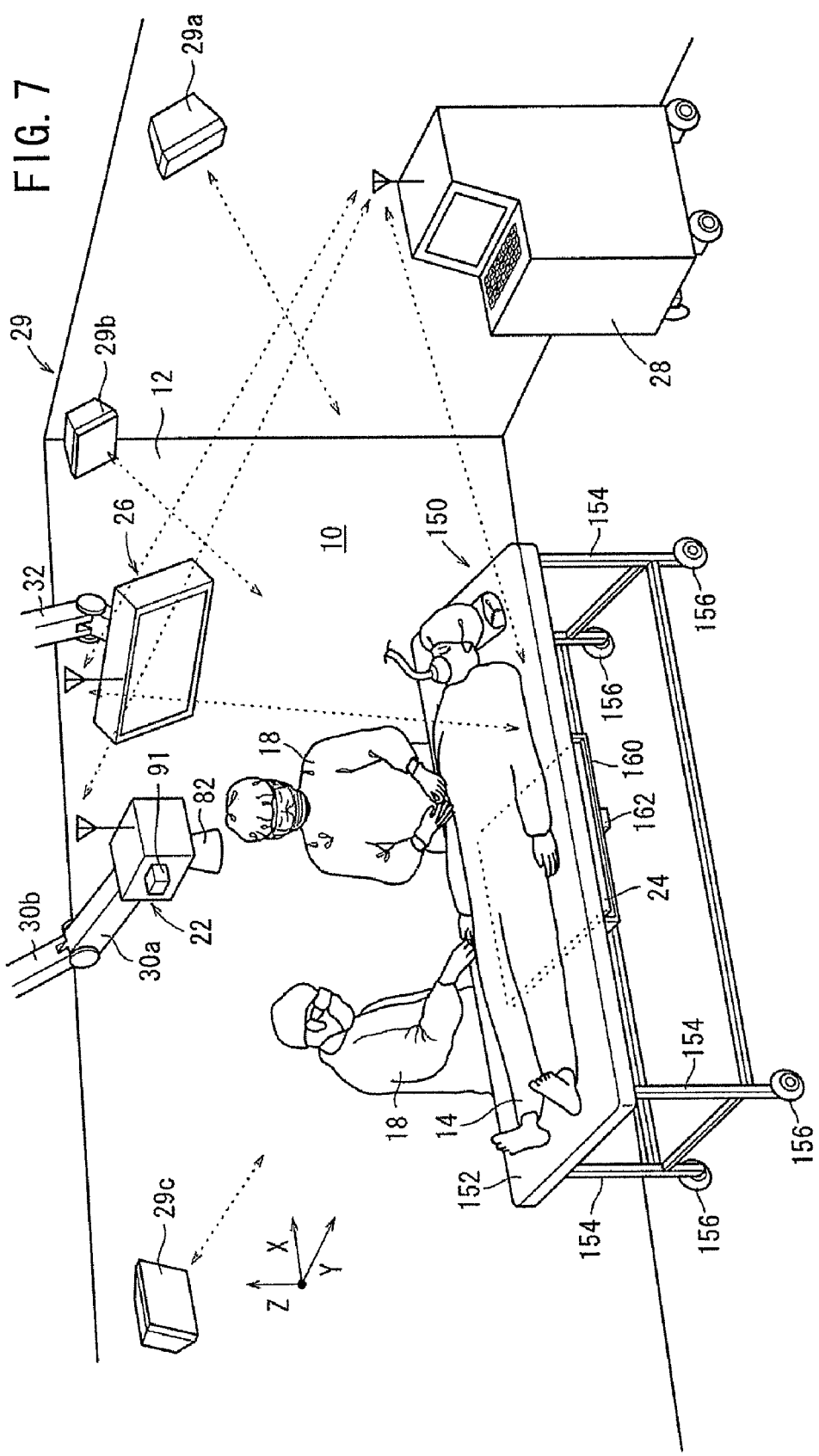
FIG. 7 is a perspective view inside the operating room incorporating the radiation image capturing system shown in FIG. 1, with the surgical table being replaced with a movable stretcher which can accommodate therein a radiation detecting cassette according to another embodiment of the present invention.
Figure 8:
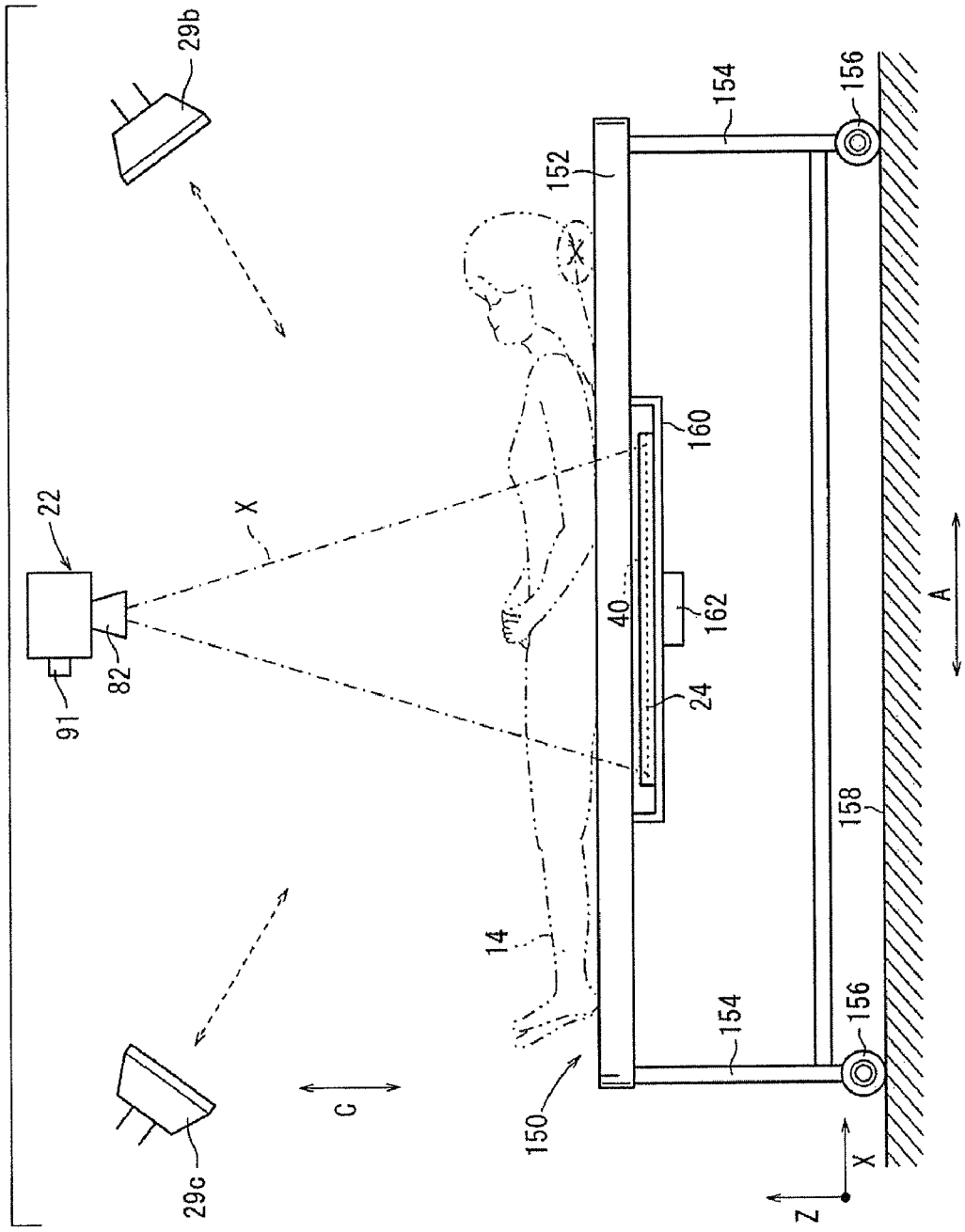
FIG. 8 is a side elevational view of the movable stretcher with the patient lying thereon in the operating room shown in FIG. 7.
Figure 9:
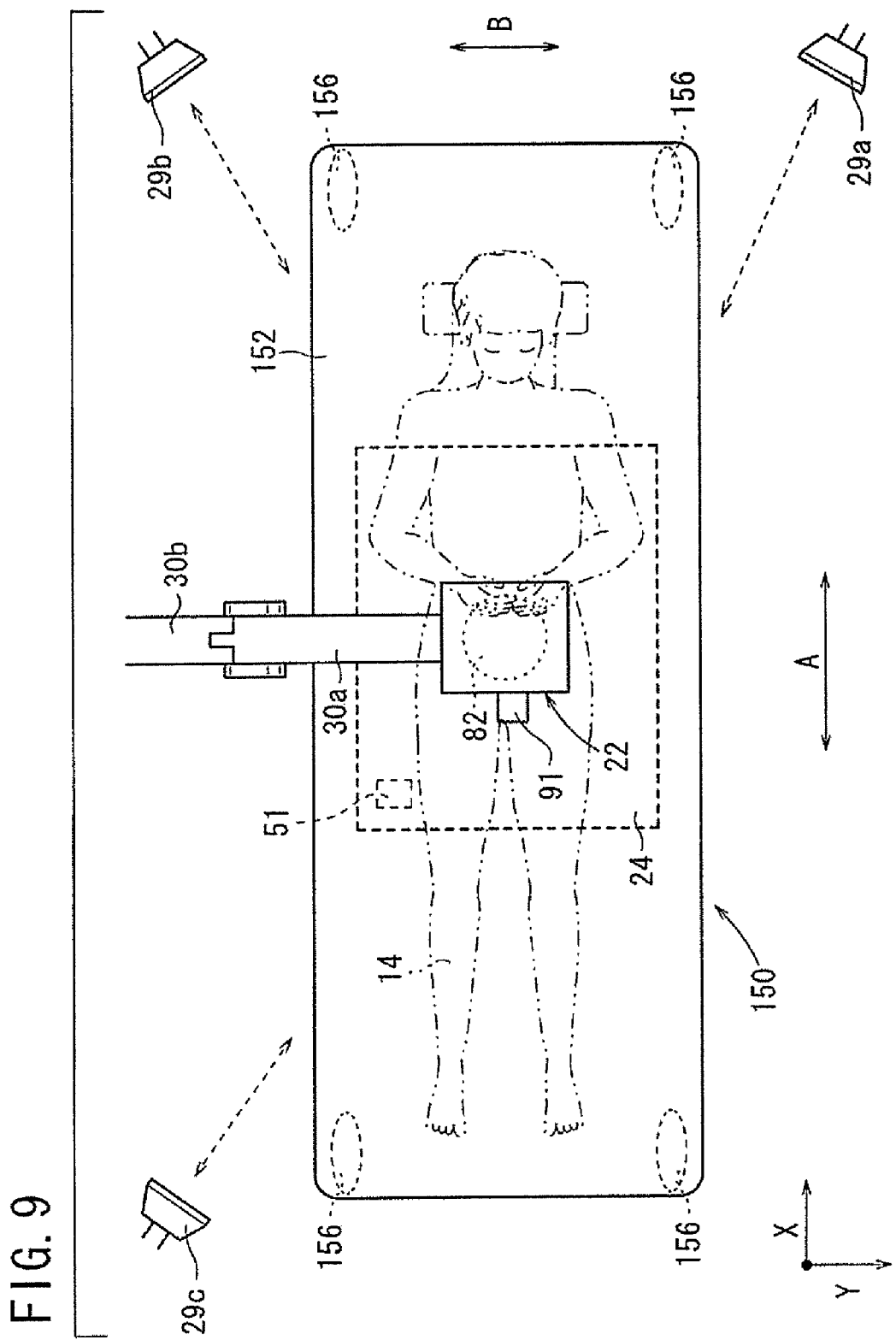
FIG. 9 is a plan view of the movable stretcher with the patient lying thereon in the operating room shown in FIG. 7.

As shown in FIGS. 7 through 9, the stretcher 150 comprises a bed 152 for the patient 14 to lie on an upper surface thereof, four legs 154 extending downwardly from the respective four corners of the bed 152, and casters 156 rotatably mounted on the respective lower ends of the legs 154. The casters 156 are rotatable on a floor 158 to move the bed 152 with the patient 14 lying thereon.

The bed 152 has a cassette holder 160 mounted on a lower surface thereof for housing the radiation detecting cassette 24 therein. The cassette holder 160 mounted on the lower surface of the bed 152 faces the floor 158 and has a space therein which is open laterally of the bed 152. The cassette holder 160 is movable along the bed 152 in the longitudinal directions thereof indicated by the arrow A, with the radiation detecting cassette 24 being housed in the space thereof. The position of the cassette holder 160, i.e., the radiation detecting cassette 24 with respect to the bed 152 can be changed depending on the area of the patient 14 to be imaged.

The cassette holder 160 has a third receiver (position detecting unit) 162 mounted centrally on a lower surface thereof for receiving radio waves emitted from the antenna device 29.

For capturing a radiation image of the patient 14, the cassette holder 160 is positionally adjusted to a position vertically aligned with the area of the patient 14 to be imaged, and then the stretcher 150 with the patient 14 lying thereon is moved into the operating room 12. The first, second, and third transceivers 29a, 29b, 29c of the antenna device 29 emit radio waves, which are received by the second receiver 91 mounted on the image capturing apparatus 22 and the third receiver 162 mounted on the cassette holder 160.

The position determining unit 124 of the console 28 calculates the propagation times "t" of the radio waves emitted from the respective the first, second, and third transceivers 29a, 29b, 29c, from the time the radio waves are emitted until they are received by the second and third receivers 91, 162, and specifies the positions of the second and third receivers 91, 162 in the operating room 12 based on the differences between the propagation times "t".

Then, based on the positions of the image capturing apparatus 22 and the cassette holder 160 in the operating room 12, the position determining unit 124 calculates the relative positions of the image capturing apparatus 22 having the second receiver 91 and the cassette holder 160 having the third receiver 162, and determines whether or not the image capturing apparatus 22 is positioned upwardly of the cassette holder 160 in vertically head-on facing relation thereto.

If the position determining unit 124 confirms that the image capturing apparatus 22 is positioned upwardly of the cassette holder 160 in vertically head-on facing relation thereto, then the radiation detecting cassette 24 is inserted into the cassette holder 160, and a radiation image of the patient 14 is captured in the radiation detecting cassette 24.

If the position determining unit 124 judges that the image capturing apparatus 22 is not positioned upwardly of the cassette holder 160 in vertically head-on facing relation thereto, then the position determining unit 124 gives the console 28, the display device 26, etc. a warning indicating that the image capturing apparatus 22 and the cassette holder 160 are not placed in the desired position.

Accordingly, the cassette holder 160 and the image capturing apparatus 22 can be placed in head-on facing relation to each other before the radiation detecting cassette 24 is inserted into the cassette holder 160. Therefore, it is possible to confirm quickly whether the image capturing apparatus 22 is positioned upwardly of the cassette holder 160 in vertically head-on facing relation thereto irrespectively of whether or not the radiation detecting cassette 24 is installed in position at the time the stretcher 150 is brought into the operating room 12.

The radiation detecting cassette 24 may be inserted into the cassette holder 160 before the stretcher 150 is brought into the operating room 12. If the radiation detecting cassette 24 is inserted into the cassette holder 160 before the stretcher 150 is brought into the operating room 12, then it is determined whether or not the image capturing apparatus 22, the radiation detecting cassette 24, and the cassette holder 160 are positioned in vertically head-on facing relation to each other based on the radio waves emitted from the first, second, and third transceivers 29a, 29b, 29c.

Still another example of the first embodiment will be described below with reference to FIGS. 10 and 11. According to the still other example, a surgical table 200 with the radiation detecting cassette 24 being placed on one side thereof is installed in the operating room 12 incorporating the radiation image capturing system 10 shown in FIG. 1.

Figure 10:
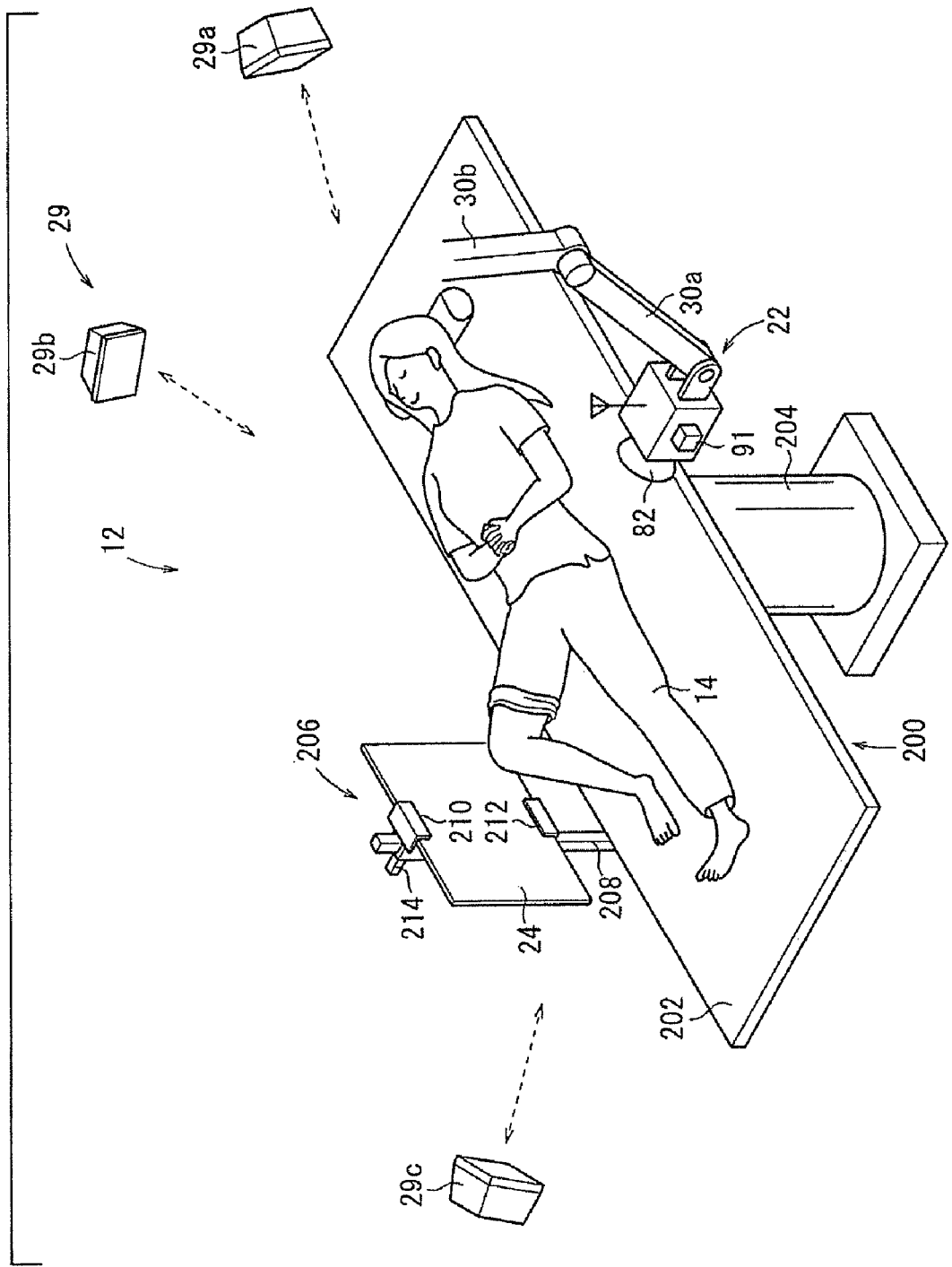
FIG. 10 is a schematic perspective view inside the operating room including a surgical table which is capable of holding a radiation detecting cassette on one side thereof according to still another embodiment of the present invention.
Figure 11:
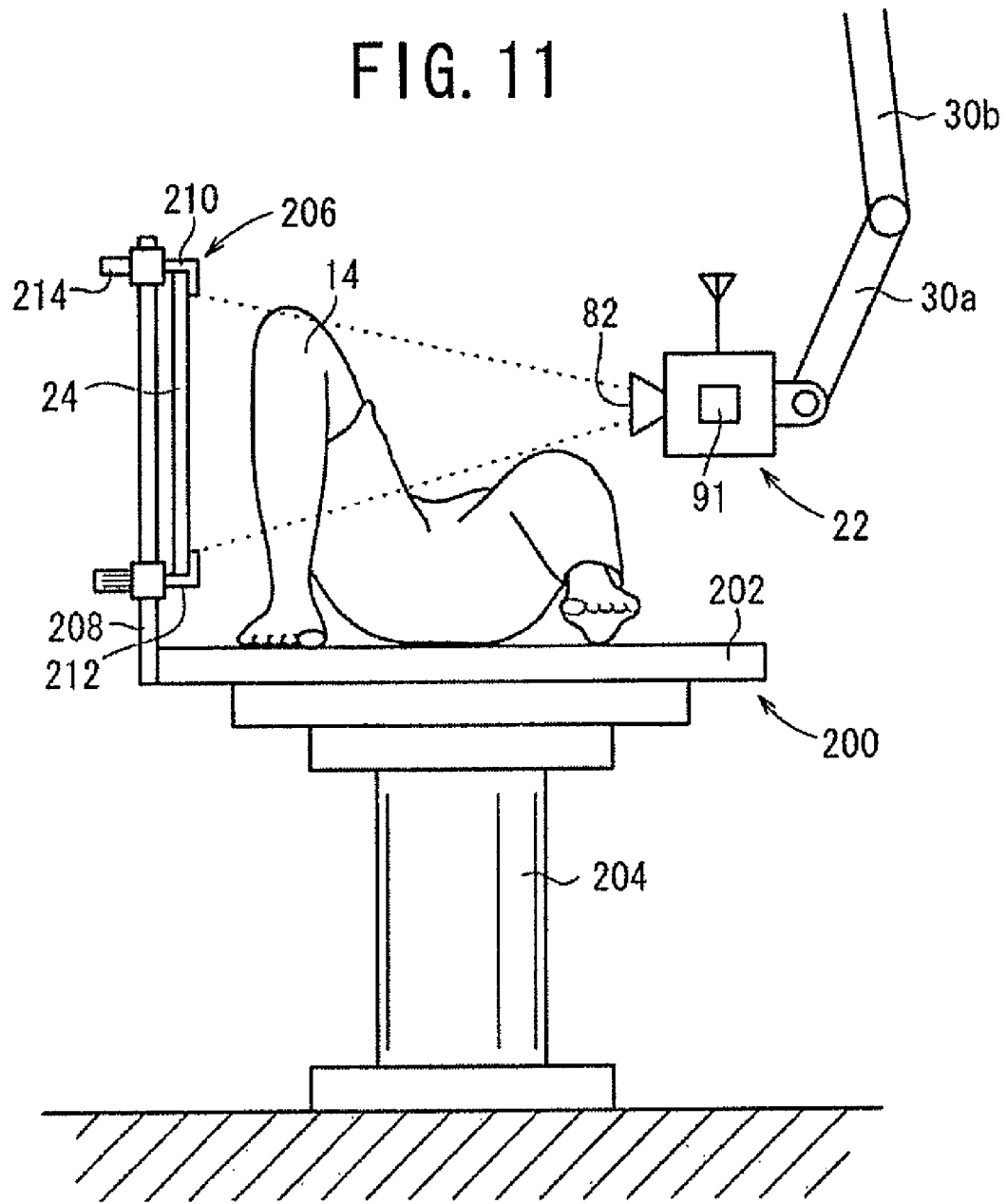
FIG. 11 is an end elevational view of the operating room shown in FIG. 10 as viewed from the feet of the patient.

As shown in FIGS. 10 and 11, the surgical table 200 comprises a bed 202 for the patient 14 to lie on an upper surface thereof, a leg 204 erected from the floor and supporting the bed 202 on its upper end, and a cassette holder 206 mounted on one side of the bed 202 for holding the radiation detecting cassette 24.

The cassette holder 206 comprises a post 208 fixed to the side of the bed 202 and extending upwardly perpendicularly to the horizontal plane of the bed 202, a first holder 210 mounted on an upper portion of the post 208, a second holder 212 displaceably mounted on a lower portion of the post 208, and a fourth receiver (position detecting unit) 214 mounted on an upper end of the post 208 for receiving radio waves emitted from the antenna device 29. The radiation detecting cassette 24 is held by the cassette holder 206 as follows: The radiation detecting cassette 24 is positioned between the first and second holders 210, 212 in front of the post 208, and has an upper edge held against the first holder 210. Then, the second holder 212 is displaced along the post 208 into abutment against a lower edge of the radiation detecting cassette 24, whereupon the radiation detecting cassette 24 is gripped between the first and second holders 210, 212.

For capturing a radiation image of the patient 14, the cassette holder 206 is positionally adjusted to a position horizontally aligned with the area of the patient 14 (e.g., a knee region) to be imaged. The first, second, and third transceivers 29a, 29b, 29c of the antenna device 29 emit radio waves, which are received by the second receiver 91 mounted on the image capturing apparatus 22 and the fourth receiver 214 of the cassette holder 206. The position determining unit 124 of the console 28 calculates the propagation times "t" of the radio waves emitted from the respective the first, second, and third transceivers 29a, 29b, 29c, from the time the radio waves are emitted until they are received by the second and fourth receivers 91, 214, and specifies the positions of the second and fourth receivers 91, 214 in the operating room 12 based on the differences between the propagation times "t".

Then, based on the positions of the image capturing apparatus 22 and the cassette holder 206 in the operating room 12, the position determining unit 124 calculates the relative positions of the image capturing apparatus 22 having the second receiver 91 and the cassette holder 206 having the fourth receiver 214, and determines whether or not the image capturing apparatus 22 is positioned laterally of the cassette holder 206 in horizontally head-on facing relation thereto.

If the position determining unit 124 confirms that the image capturing apparatus 22 is positioned laterally of the cassette holder 206 in horizontally head-on facing relation thereto, then the radiation detecting cassette 24 is set on the cassette holder 206, and a radiation image of the patient 14 is captured in the radiation detecting cassette 24.

If the position determining unit 124 judges that the image capturing apparatus 22 is not positioned laterally of the cassette holder 206 in horizontally head-on facing relation thereto, then the position determining unit 124 gives the console 28, the display device 26, etc. a warning indicating that the image capturing apparatus 22 and the cassette holder 206 are not placed in the desired position.

Accordingly, the cassette holder 206 and the image capturing apparatus 22 can be placed in head-on facing relation to each other before the radiation detecting cassette 24 is set on the cassette holder 206. Therefore, it is possible to confirm quickly whether the image capturing apparatus 22 is positioned laterally of the cassette holder 206 in horizontally head-on facing relation thereto irrespectively of whether the radiation detecting cassette 24 is set on the cassette holder 206.

The radiation detecting cassette 24 may be set on the cassette holder 206 before the image capturing apparatus 22 and the cassette holder 206 are brought into head-on facing relation to each other. If the radiation detecting cassette 24 are set on the cassette holder 206 before the image capturing apparatus 22 and the cassette holder 206 are brought into head-on facing relation to each other, then it is determined whether or not the image capturing apparatus 22, the radiation detecting cassette 24, and the cassette holder 206 are positioned in horizontally head-on facing relation to each other based on the radio waves emitted from the first, second, and third transceivers 29*a*, 29*b*, 29*c*.

When the radiation detecting cassette 24 is used in the operating room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the operating room 12, and may be used for a medical examination and a round in the hospital.

Also, the radiation detecting cassette 24 may communicate with external devices via optical wireless communication using infrared light or the like, instead of general wireless communication using radio wave.

Figure 12:
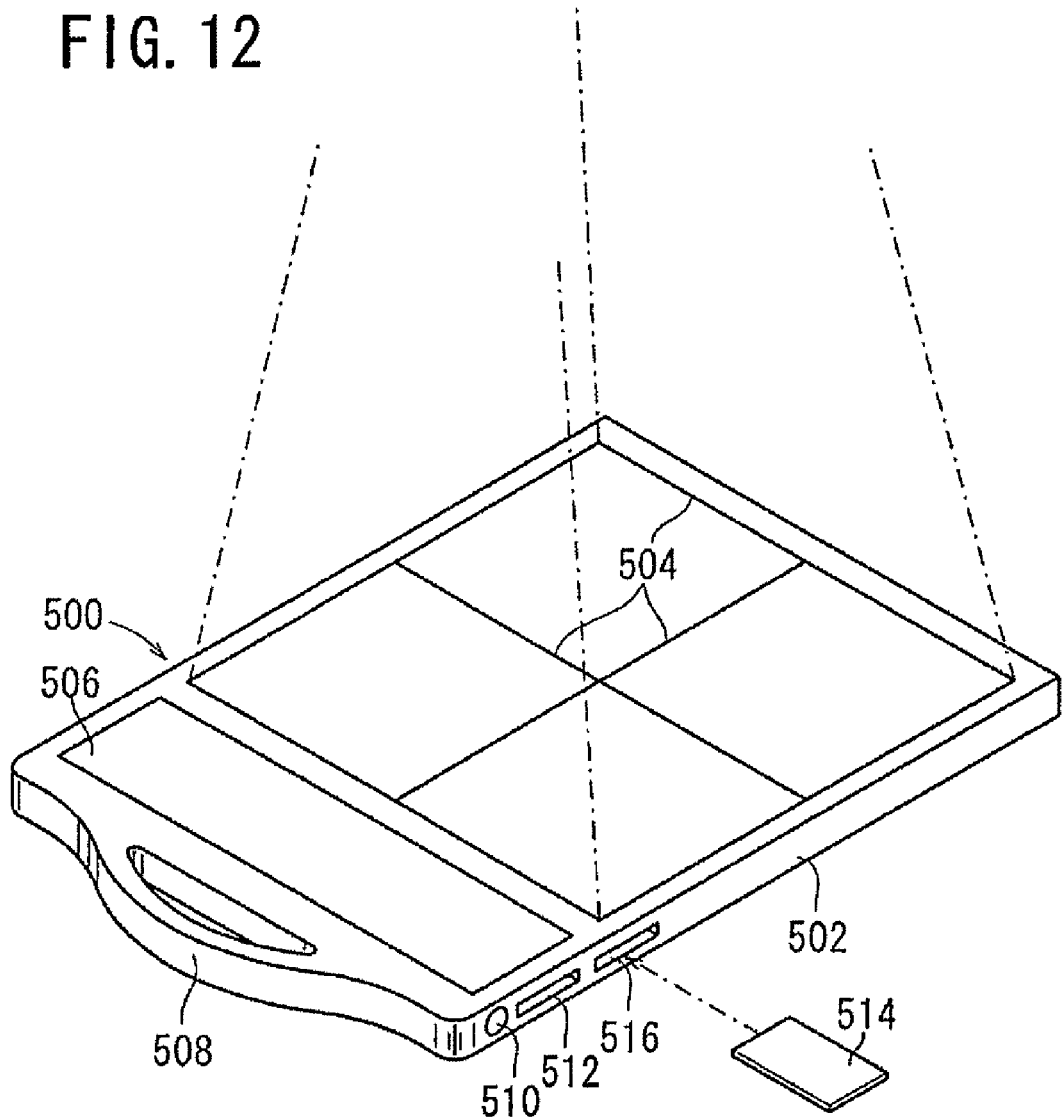
FIG. 12 is a perspective view showing a radiation detecting cassette according to further still another embodiment of the present invention.

Preferably, the radiation detecting cassette 500 may be constructed as shown in FIG. 12.

Specifically, the radiation detecting cassette 500 includes a guiding line 504 drawn on the radiation-irradiated surface of a casing 502, the guiding line 504 serving as a reference for setting a captured area and a captured position. Using the guiding line 504, a subject can be positioned with respect to the radiation detecting cassette 500, and an area irradiated with the radiation can be set, thereby recording radiation image information on an appropriate captured area.

The radiation detecting cassette 500 is provided with a display section 506 on an area thereof other than the captured area, for displaying various information about the radiation detecting cassette 500. The information which is displayed on the display section 506, includes ID information of a subject whose radiation image information is to be recorded on the radiation detecting cassette 500, the number of times the radiation detecting cassette 500 has been used, an accumulated exposed radiation dose, a charging state (remaining battery level) of a battery 44 in the radiation detecting cassette 500, image capturing conditions of radiation image information, and a positioning image of the subject with respect to the radiation detecting cassette 500. In this case, a technician confirms a subject based on the ID information displayed on the display section 506, for example, and also previously confirms that the radiation detecting cassette 500 is placed in a usable state. Then, the technician positions a desired captured area of the subject with respect to the radiation detecting cassette 500 based on the displayed positioning image, thereby capturing appropriate radiation image information.

Also, the radiation detecting cassette 500 is provided with a handgrip 508, whereby it is easier to handle and carry the radiation detecting cassette 500.

Preferably, the radiation detecting cassette 500 may have, on a side thereof, an input terminal 510 for an AC adapter, a USB (Universal Serial Bus) terminal 512, and a card slot 516 for inserting a memory card 514.

When the charging function of the battery 44 in the radiation detecting cassette 500 becomes deteriorated, or when there is not enough time to fully charge the battery 44, the input terminal 510 is connected to the AC adapter to externally supply the radiation detecting cassette 500 with electric power, thereby enabling the radiation detecting cassette 500 to be used immediately.

The USB terminal 512 or the card slot 516 may be used when the radiation detecting cassette 500 cannot transmit and receive information to and from external devices such as the console 28 via wireless communication. Specifically, by connecting a cable to the USB terminal 512, the radiation detecting cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 13:
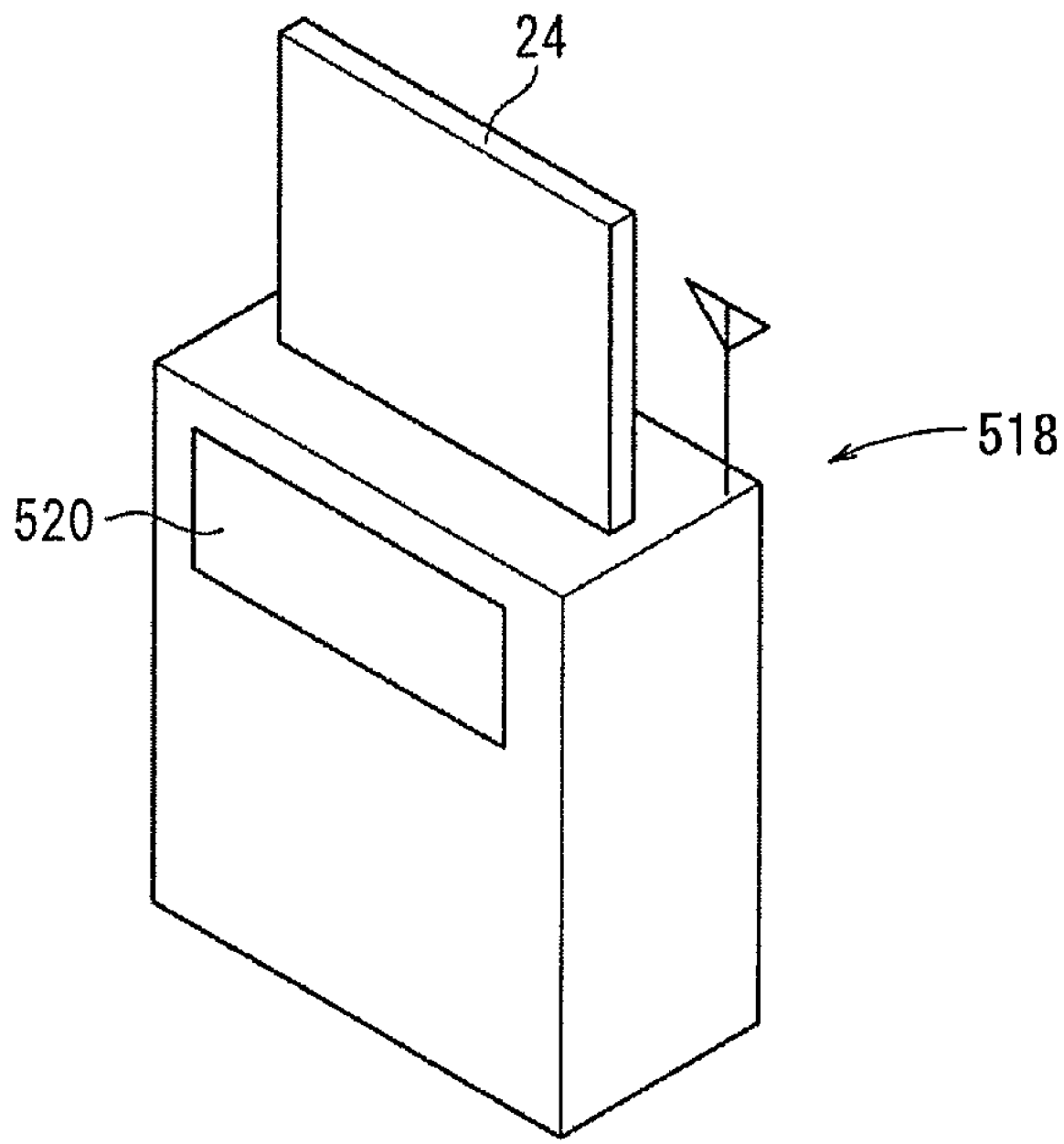
FIG. 13 is a perspective view showing a cradle which charges the radiation detecting cassette.

Preferably, a cradle 518 may be disposed in the operating room 12 or at a desired place in the hospital, into which the radiation detecting cassette 24 is inserted to charge the internal battery 44, as shown in FIG. 13. In this case, in addition to charging the battery 44, the cradle 518 may transmit and receive necessary information to and from external devices such as HIS, RIS, the console 28, etc. by way of wireless or wire communications of the cradle 518. The information may include radiation image information which is recorded on the radiation detecting cassette 24 inserted into the cradle 518.

Also, the cradle 518 may be provided with a display section 520. The display section 520 may display necessary information including a charging state of the inserted radiation detecting cassette 24 and radiation image information acquired from the radiation detecting cassette 24.

Further, a plurality of cradles 518 may be connected to a network. In this case, information about charging states of radiation detecting cassettes 24 inserted in respective cradles 518 can be collected through the network, and the radiation detecting cassette 24 in a usable state can be located.

For example, the aforementioned radiation detector (radiation conversion panel) 40 makes up a direct-conversion type of radiation detector, which converts the radiation dose of the irradiated radiation directly into electric signals through the photoelectric conversion layer 59. However, in place of this structure, a indirect-conversion type of radiation detector in which irradiated radiation is converted initially into visible light by a scintillator, and thereafter, the visible light is converted into electric signals using a solid-state detecting device formed from amorphous silicon (a-Si) or the like, may also be used (see, Japanese Patent No. 3494683).

Next, with reference to FIGS. 14 to 19, a radiation image capturing system 600 according to a second embodiment of the invention shall be explained. Structural elements thereof which are the same as those of the radiation image capturing system 10 according to the above-described first embodiment are designated with the same reference numerals and detailed explanations of such features shall be omitted.

Figure 14:
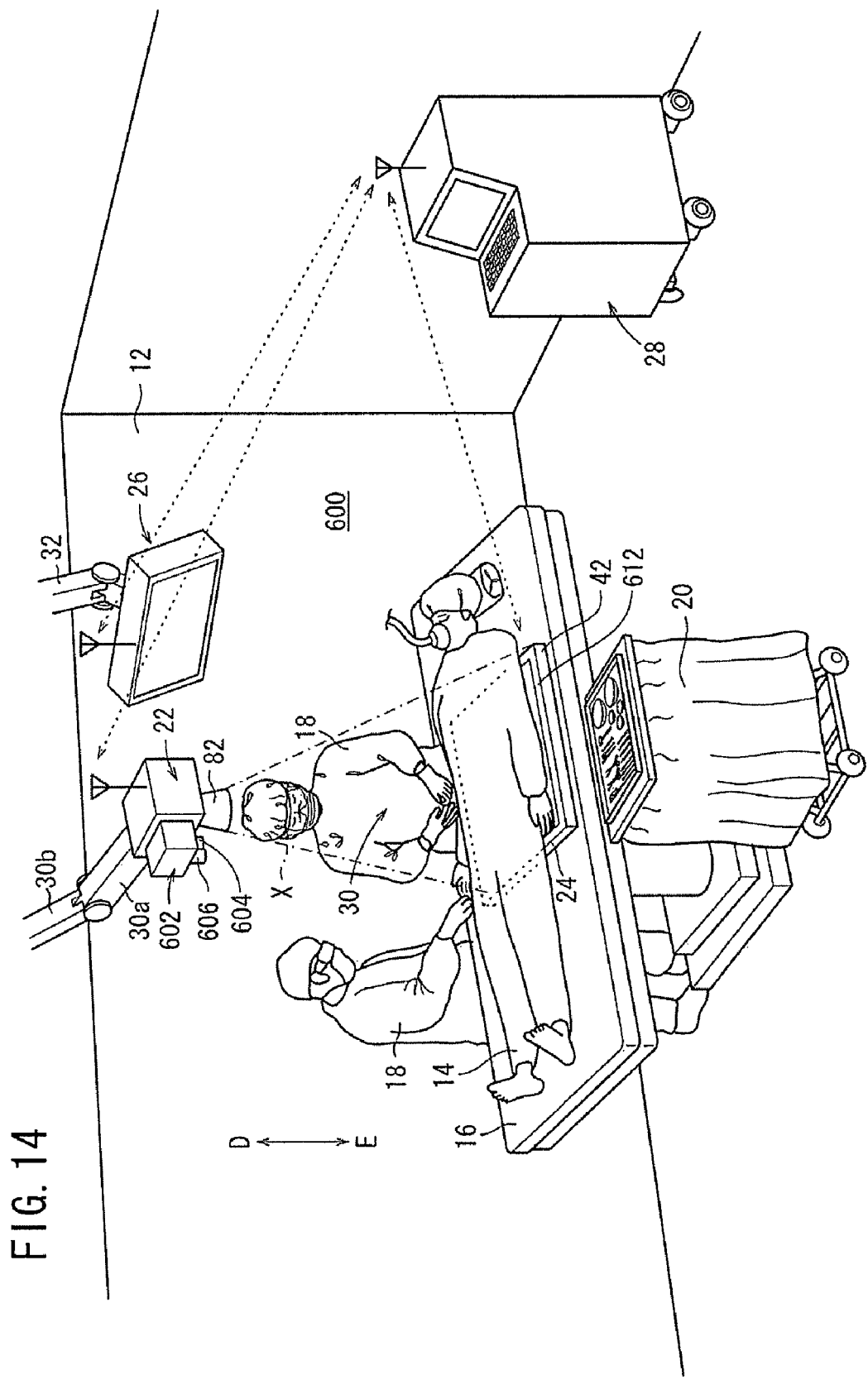
FIG. 14 is a perspective view inside an operating room incorporating a radiation image capturing system according to a second embodiment of the present invention.
Figure 15:
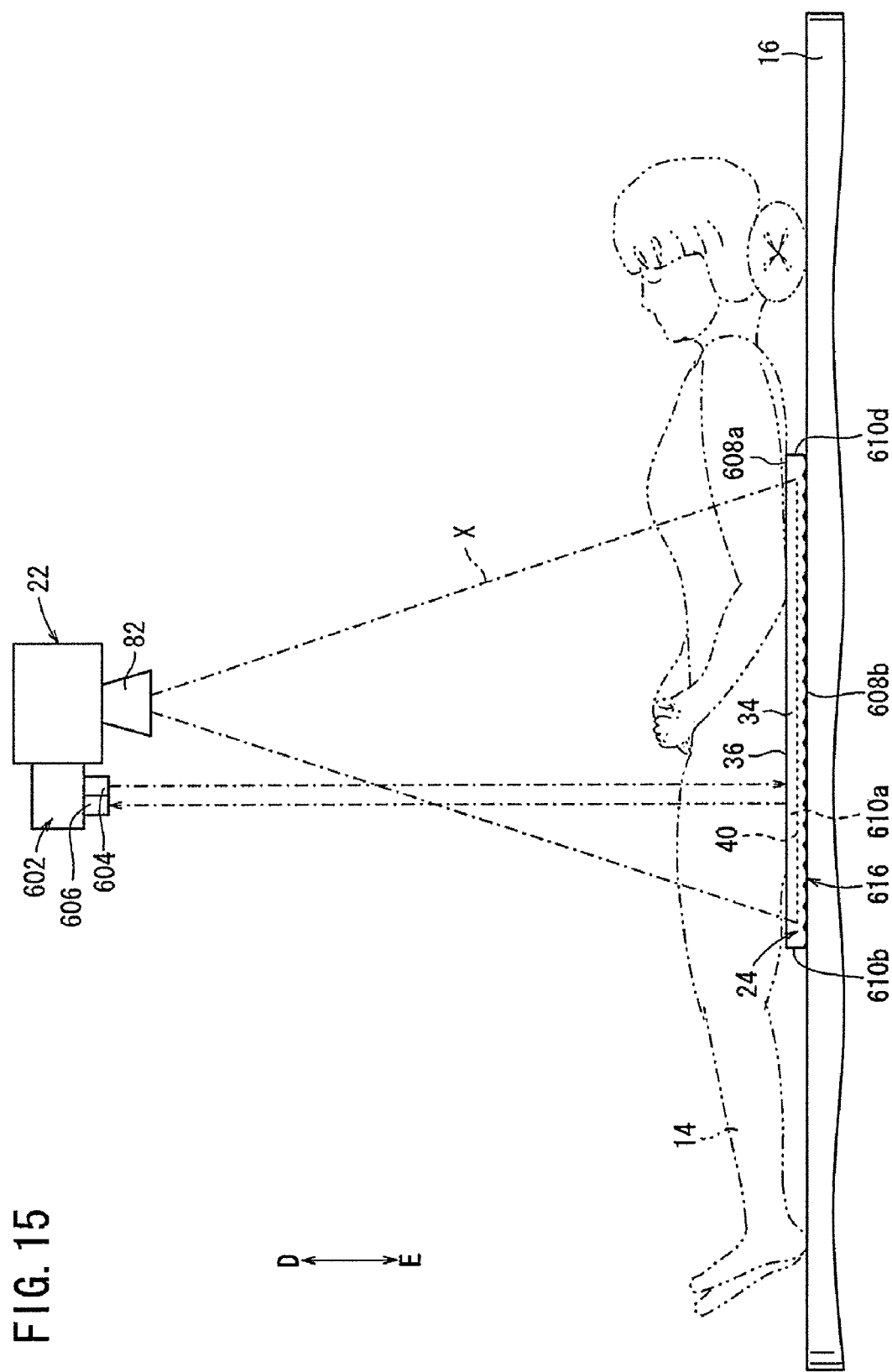
FIG. 15 is an enlarged side view showing the vicinity of a patient and a radiation detecting cassette in the operating room shown in FIG. 14.

The radiation image capturing system 600 includes, as shown in FIG. 14, an orientation detecting unit 602 for detecting a direction of the radiation detecting cassette 24 with respect to the image capturing apparatus 22, the orientation detecting unit 602 being mounted on a side of the image capturing apparatus 22 so as to face the radiation detecting cassette 24 set on the surgical table 16.

The orientation detecting unit 602 comprises, for example, a reflection type photosensor having a light-emitting part 604 for emitting light and a light-receiving part 606 for receiving the emitted light. The light-emitting part 604 and the light-receiving part 606 are directed so as to face the radiation detecting cassette 24 (see FIG. 15).

The light-emitting part 604 emits light toward the radiation detecting cassette 24 substantially orthogonally, and the light-receiving part 606 receives the emitted light reflected by the irradiated surface 36 of the radiation detecting cassette 24. The detection results obtained by the orientation detecting unit 602 is output to a transceiver of the image capturing apparatus 22, and then transmitted to the console 28. The orientation detecting unit 602 may be disposed inside the image capturing apparatus 22.

On the other hand, the radiation detecting cassette 24 comprises a reflection portion 612 having a predetermined width on a flat plate portion 608*a* including the irradiated surface 36 of the casing 34 irradiated with the radiation X, along the ends of the flat plate portion 608*a* near the walls 610*a* to 610*d* of the casing 34. The reflection portion 612 is made of, for example, a recursively reflective material. The reflection portion 612 is formed into a sheet shape and attached to the flat plate portion 608*a* such that the reflection portion 612 reflects the light emitted from the light-emitting part 604 toward the orientation detecting unit 602 (in the direction indicated by the arrow D). That is, the reflection portion 612 has a frame shape surrounding the flat plate portion 608*a* (see FIG. 16).

Figure 17:
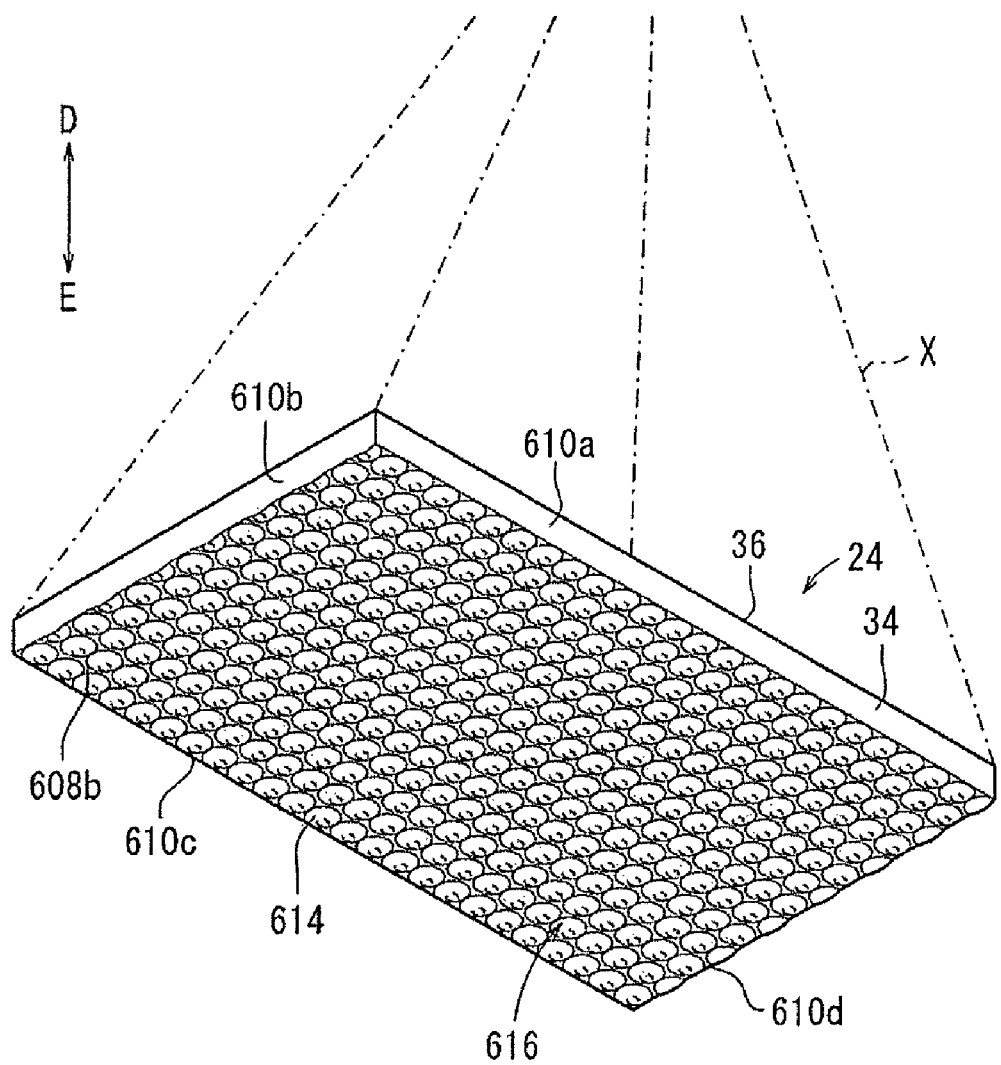
FIG. 17 is a perspective view of the radiation detecting cassette shown in FIG. 16, as viewed from the rear side.
Figure 18:
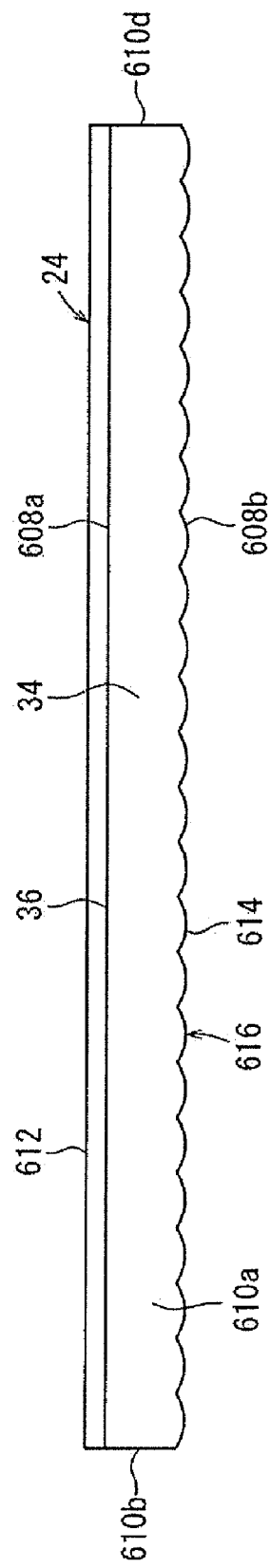
FIG. 18 is a side view of the radiation detecting cassette.

On a rear plate portion 608*b* of the casing 34 on the opposite side of the irradiated surface 36, as shown in FIGS. 17 and 18, a scattering portion 616 having an uneven surface with a plurality of expanded faces 614 is formed. When the radiation detecting cassette 24 is placed such that the rear plate portion 608*b* having the scattering portion 616 faces the image capturing apparatus 22 and the orientation detecting unit 602, the scattering portion 616 scatters the light emitted from the orientation detecting unit 602.

The scattering portion 616 is formed along the surface of the rear plate portion 608*b*. Each of the expanded faces 614 has a substantially arcuate shape in cross section and expands outwardly from the casing 34 (in the direction indicated by the arrow E).

That is, the casing 34 includes the reflection portion 612 that is formed on the flat plate portion 608*a* facing the patient 14 and the image capturing apparatus 22 and irradiated with the radiation X. The casing 34 also includes the scattering portion 616 that is formed on the rear plate portion 608*b* facing the surgical table 16 on which the patient 14 is lying. In other words, the reflection portion 612 is formed on the flat plate portion 608*a* closer to the radiation detector 40 irradiated with the radiation X, and the scattering portion 616 is formed on the rear plate portion 608*b* on the side of the lead plate 42 which absorbs back scattered rays from the radiation X (in the direction indicated by the arrow E).

Figure 16:
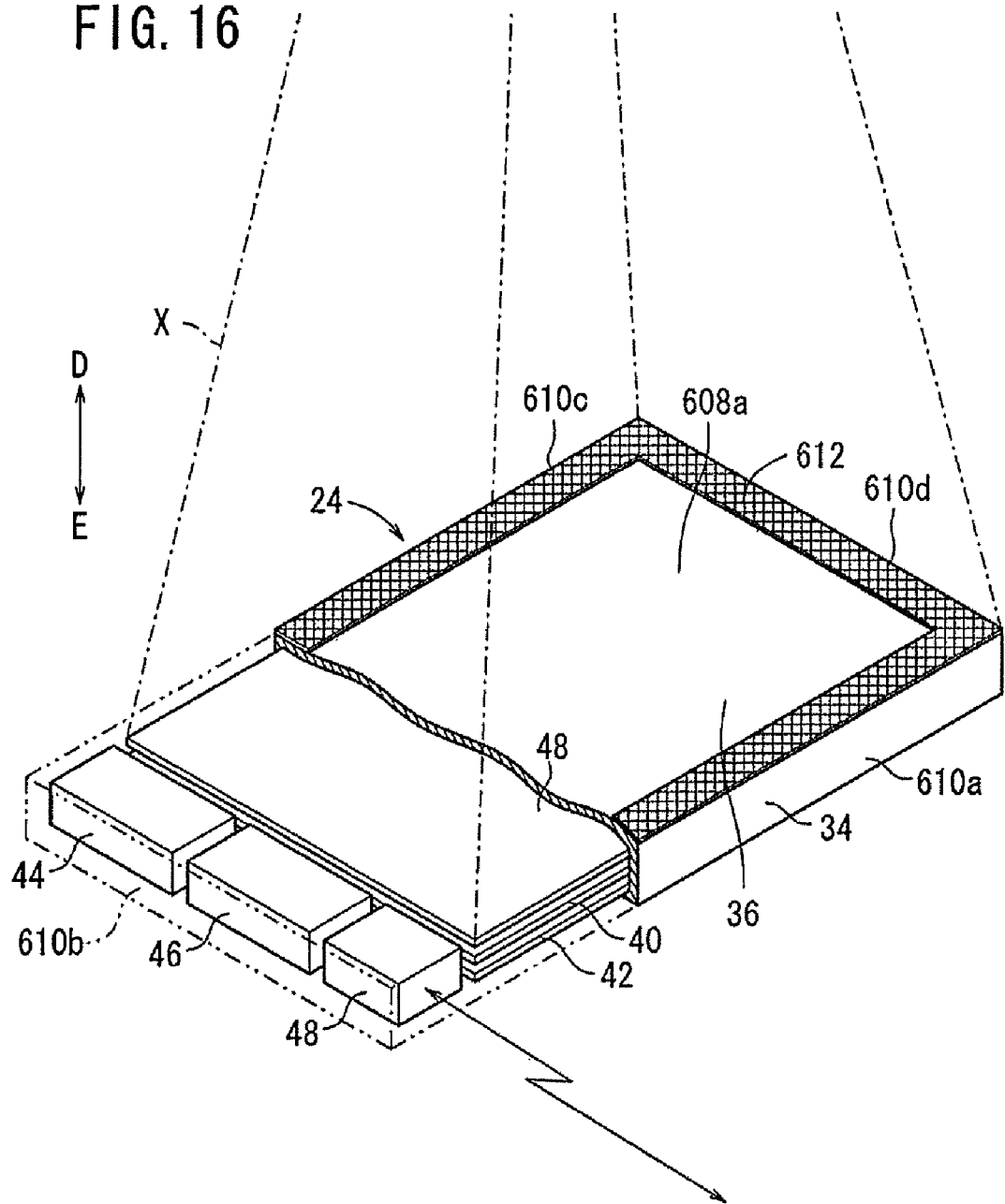
FIG. 16 is a perspective view, partly cut away, of the radiation detecting cassette used in the radiation image capturing system, as viewed from the irradiation side.
Figure 19A:
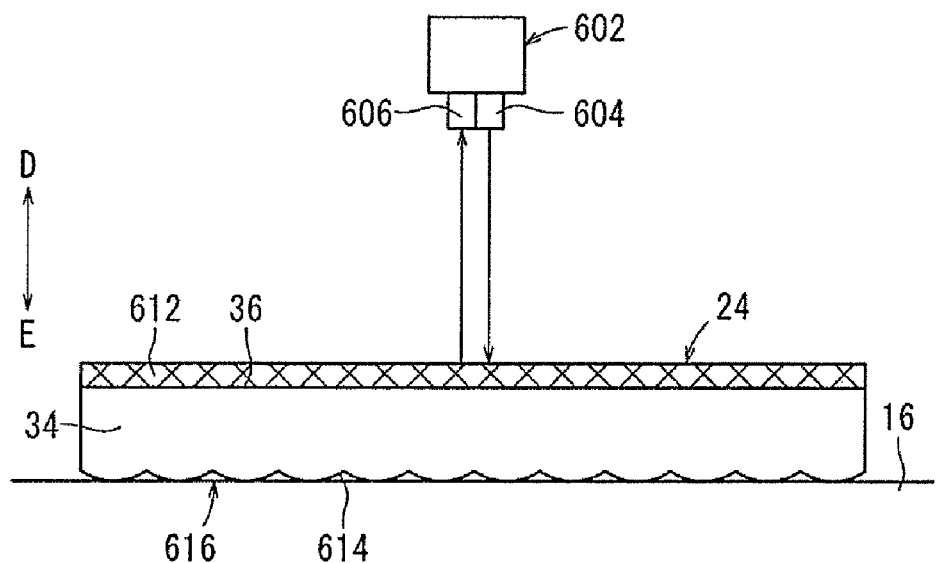
FIG. 19A is a side view showing a state in which a irradiated surface of the radiation detecting cassette faces an image capturing apparatus and an orientation detecting unit.

In the radiation image capturing system 600 according to the second embodiment, as shown in FIGS. 16 and 19A, the light-emitting part 604 of the orientation detecting unit 602 emits light toward the radiation detecting cassette 24 (in the direction indicated by the arrow E), the reflection portion 612 formed on the casing 34 reflects the emitted light, and the reflected light returns toward the orientation detecting unit 602 (in the direction indicated by the arrow D) so as to allow the light-receiving part 606 to receive the reflected light. Specifically, a part of reflection portion 612 which is not covered by the patient 14 reflects the emitted light to the light-receiving part 606 (in the direction indicated by the arrow D). That is, the reflection portion 612 is formed on the flat plate portion 608*a* near the walls 610*a* to 610*d* of the casing 34 in order to avoid the patient 14 lying on the irradiated surface 36.

Then, based on the detection results obtained by the orientation detecting unit 602, a detection signal is output to the transceiver in the image capturing apparatus 22. Thereafter, the detection signal is further output to a status determination unit (not shown) through the transceiver of the console 28.

The status determination unit confirms, based on the detection signal, that the light emitted from the light-emitting part 604 is received by the light-receiving part 606, and determines that the flat plate portion 608*a* having the reflection portion 612 of the casing 34 faces the orientation detecting unit 602. That is, the status determination unit confirms that the radiation detecting cassette 24 is placed such that the irradiated surface 36 faces toward the image capturing apparatus 22 (in the direction indicated by the arrow D).

Figure 19B:
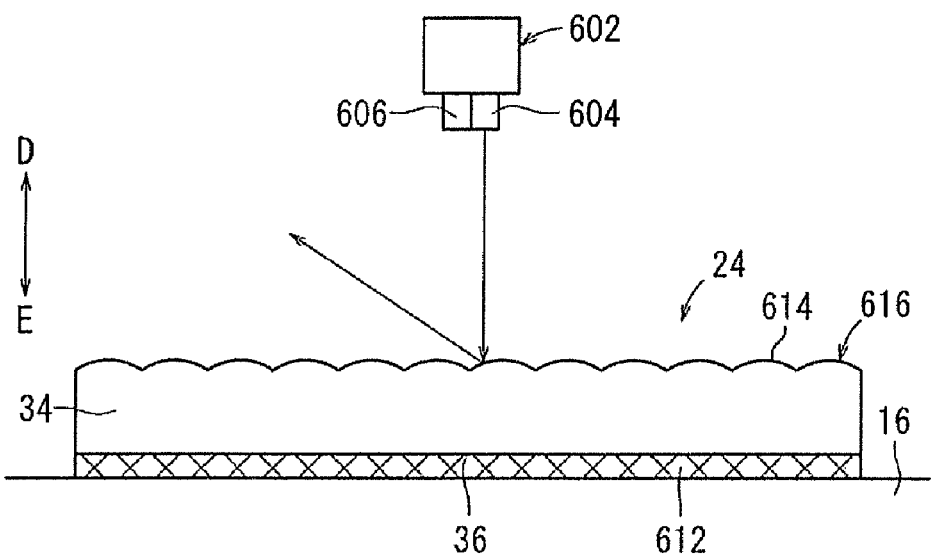
FIG. 19B is a side view showing a state in which a rear surface of the radiation detecting cassette faces the image capturing apparatus and the orientation detecting unit.

On the other hand, as shown in FIG. 19B, if the radiation detecting cassette 24 is inadvertently placed so that the rear plate portion 608*b* having the scattering portion 616 faces toward the patient 14 and the image capturing apparatus 22 (in the direction indicated by the arrow D), because the light emitted from the light-emitting part 604 of the orientation detecting unit 602 travels toward the detecting cassette 24 (in the direction indicated by the arrow E) and is scattered into directions by the expanded faces 614 of the scattering portion 616, the light-receiving part 606 does not receive the scattered light. Accordingly, the orientation detecting unit 602 does not output a detection signal indicating that the light emitted from the light-emitting part 604 is received by the light-receiving part 606. As a result, it is determined that the rear plate portion 608*b* of the casing 34 having the scattering portion 616 faces the orientation detecting unit 602.

In this case, it is confirmed that the irradiated surface 36 of the radiation detecting cassette 24 does not face toward the image capturing apparatus 22 (in the direction indicated by the arrow D), and the surface opposite to the irradiated surface 36 inadvertently faces the image capturing apparatus 22.

As described above, according to the second embodiment, the radiation detecting cassette 24 is placed between the patient 14 and the surgical table 16, and the orientation detecting unit 602 disposed thereabove along with the image capturing apparatus 22 emits light to the radiation detecting cassette 24. Based on the receipt of the emitted light reflected by the radiation detecting cassette 24, whether the irradiated surface 36 of the radiation detecting cassette 24 faces toward the image capturing apparatus 22 (in the direction indicated by the arrow D) or not is detectable.

Because the radiation detecting cassette 24 has the scattering portion 616 on the rear plate portion 608*b* opposite to the irradiated surface 36, when the emitted light is not received by the orientation detecting unit 602, it is confirmed that the irradiated surface 36 is not directed to the image capturing apparatus 22 (in the direction indicated by the arrow D). As a result, based on the detection result, it is possible to reliably and easily reset the radiation detecting cassette 24 such that the irradiated surface 36 faces the image capturing apparatus 22. Thus, a desirable image capturing operation can be performed. Further, it is possible to improve operation efficiency because an image is not captured when the irradiated surface 36 of the radiation detecting cassette 24 inadvertently faces oppositely.

In addition, instead of the aforementioned orientation detecting unit 602, for example, a gravity sensor can be disposed inside the radiation detecting cassette 24. With the gravity sensor, it is possible to detect vertical direction with respect to the radiation detecting cassette 24. When an image capturing operation is performed with the patient 14 lying on the surgical table 16, it is possible with the gravity sensor to determine whether the irradiated surface 36 of the radiation detecting cassette 24 faces the image capturing apparatus 22 or not.

Next, with reference to FIGS. 20 to 23, a radiation image capturing system 700 according to a third embodiment of the invention shall be explained. Structural elements thereof which are the same as those of the radiation image capturing systems 10, 600 are designated with the same reference numerals and detailed explanations of such features shall be omitted.

Figure 21:
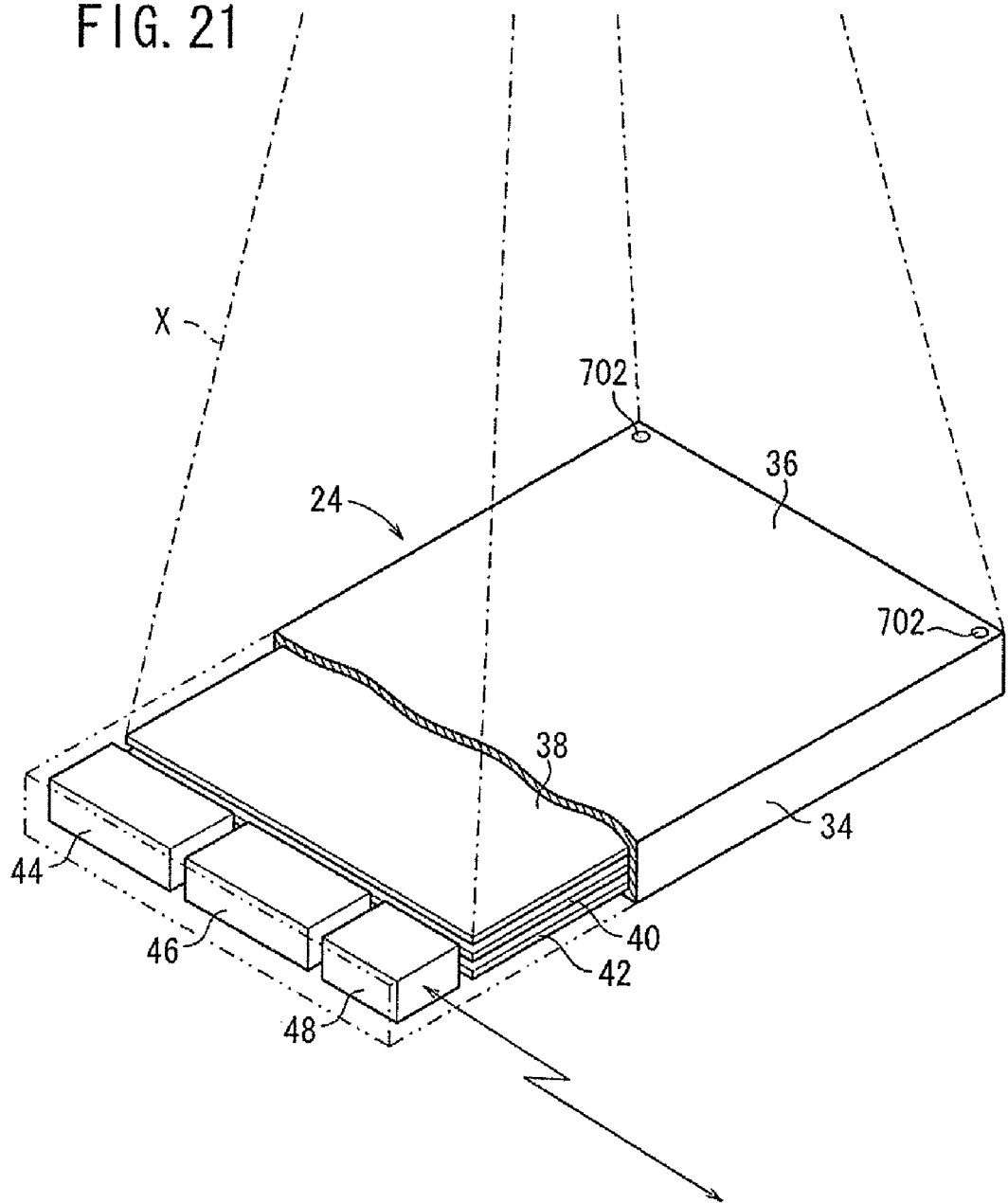
FIG. 21 is a perspective view, partly cut away, showing internal structural details of the radiation detecting cassette used in the radiation image capturing system shown in FIG. 20.

In the radiation image capturing system 700, as shown in FIGS. 20 and 21, the radiation detecting cassette 24 is placed on the surgical table 16 on which the patient 14 is lying. The grid 38, the radiation detector 40, and the lead plate 42 are not disposed in the four corners of the radiation detecting cassette 24, but signal generators 702 are disposed respectively in the four corners of the radiation detecting cassette 24. A signal detector 704 is disposed in the image capturing apparatus 22, correspondingly to the four signal generators 702 (see FIG. 22). The signal detector 704 of the image capturing apparatus 22 detects signals from the four signal generators 702 of the radiation detecting cassettes 24. Specifically, each of the signal generators 702 comprises a magnet or a magnetic generator, and the signal detector 704 comprises a three-axis magnetic field sensor for detecting a magnetic field that is generated continuously or intermittently by each of the magnets or the magnetic generators.

Figure 22:
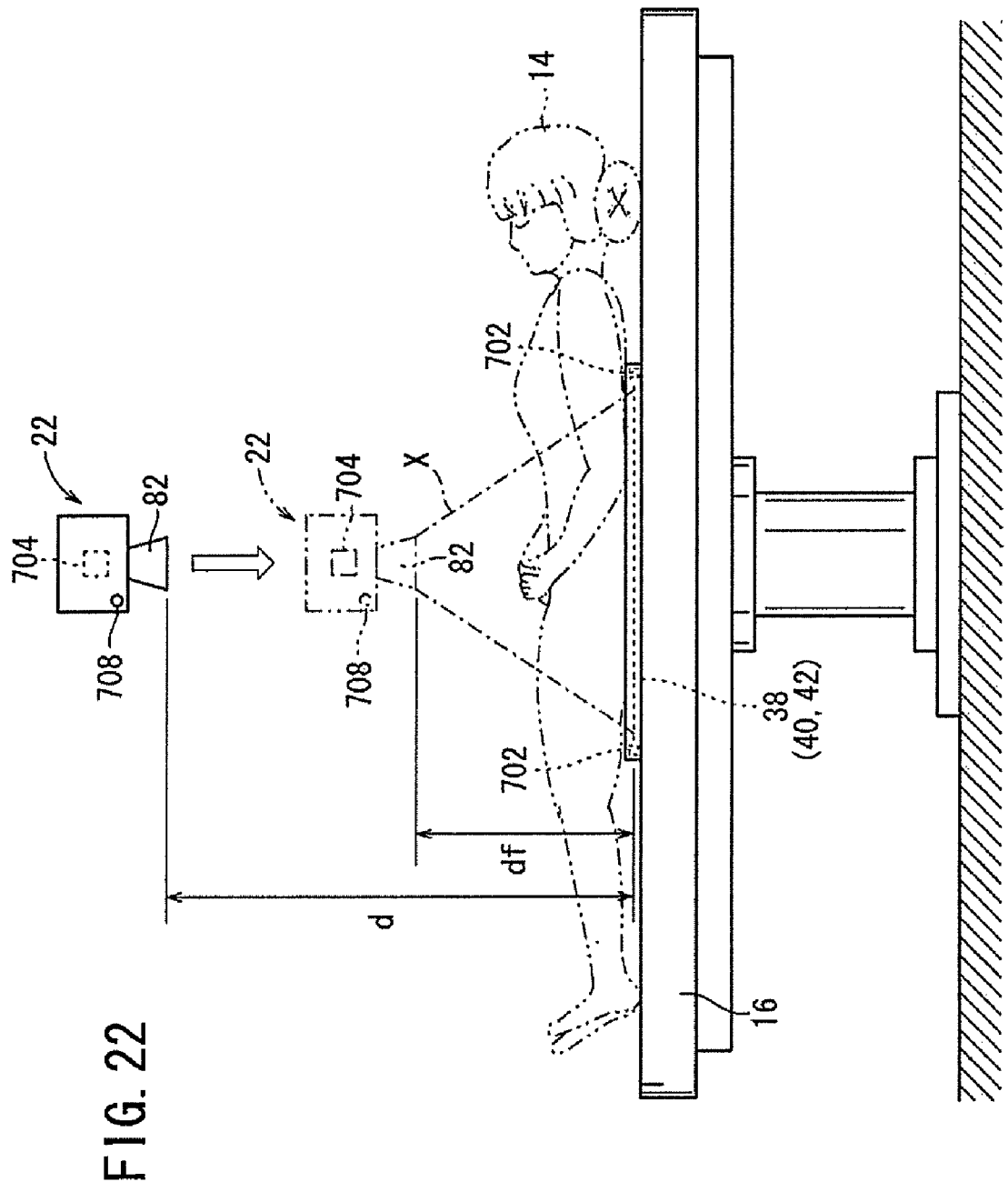
FIG. 22 is a side elevational view of a surgical table with a patient lying thereon in the operating room shown in FIG. 20.
Figure 23:
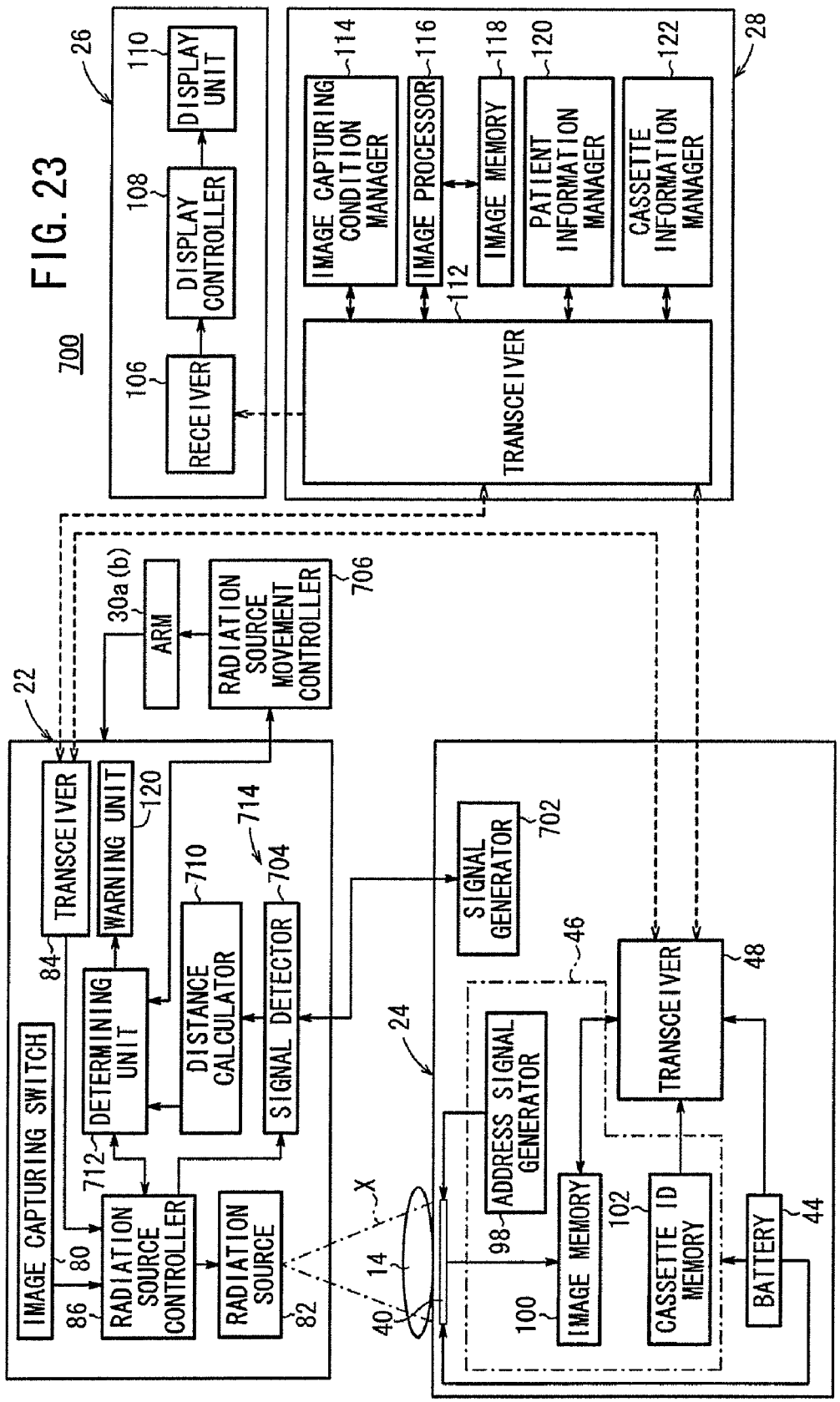
FIG. 23 is a block diagram of the radiation image capturing system shown in FIG. 20.

As shown in FIG. 22, it is assumed that the distance between the image capturing apparatus 22 and the radiation detecting cassettes 24, i.e., the distance between a radiation source 82 of the image capturing apparatus 22 and the radiation detector 40 of the radiation detecting cassettes 24 is represented by d. In the radiation image capturing system 700, the distance d is adjusted into conformity with a predetermined distance (source-to-image distance, hereinafter also referred to as "SID") df from the radiation source 82 to the radiation detector 40 at the time a radiation image of the patient 14 is to be captured. Thereafter, the image capturing apparatus 22 applies the radiation X to the patient 14.

The distance d may be adjusted when the image capturing apparatus 22 is moved to a desired position by controlling the universal arms 30a, 30b with a radiation source movement controller to be described later (see FIG. 23), or when one of the surgeons 18 or the radiological technician manually moves the universal arms 30a, 30b and the image capturing apparatus 22.

The image capturing apparatus 22 comprises an image capturing switch 80, a radiation source 82, a transceiver 84, a radiation source controller 86, a warning unit 708, a signal detector 704, a distance calculator 710, and a determining unit 712.

The radiation source controller 86 controls the radiation source 82, the signal detector 704, and the determining unit 712 based on an image capturing start signal supplied from the image capturing switch 80 and image capturing conditions supplied from the transceiver 84. The radiation source 82 outputs the radiation X under the control of the radiation source controller 86. The signal detector 704 detects signals transmitted from the signal generators 702 under the control of the radiation source controller 86.

The distance calculator 710 calculates the distance d (see FIG. 22) based on the signals from the signal generators 702 which have been detected by the signal detector 704. As described above, each of the signal generators 702 comprises a magnet or a magnetic generator, and the signal detector 704 comprises a three-axis magnetic field sensor for detecting a magnetic field that is generated continuously or intermittently by each of the magnets or the magnetic generators. Therefore, the distance calculator 710 calculates the three-dimensional positions and directions of the signal generators 702 with respect to the signal detector 704, based on the intensities of the magnetic fields detected by the magnetic sensor, and calculates the distance d from the three-dimensional positions and directions and the present position of the radiation source 82.

Thus, the signal generators 702, the signal detector 704, and the distance calculator 710 jointly serve as a distance detecting unit 714 for detecting the distance d.

Under the control of the radiation source controller 86, the determining unit 712 determines whether the distance d calculated by the distance calculator 710 matches the SID df or not. If the distance d does not match the SID df, then the determining unit 712 outputs a control signal for equalizing the distance d with the SID df to the radiation source movement controller 706. The SID df is included in the image capturing conditions that are supplied from the console 28 via transceivers 112, 84 to the radiation source controller 86.

Based on the control signal from the determining unit 712, the radiation source movement controller 706 causes the universal arms 30a, 30b to move the image capturing apparatus 22 to a predetermined position depending on the SID df until the distance d matches the SID df. After having moved the image capturing apparatus 22, the radiation source movement controller 706 outputs, to the determining unit 712, a response signal indicative of the completion of the movement of the image capturing apparatus 22.

If the determining unit 712 judges that the distance d does not match the SID df, then the determining unit 712 outputs, to the warning unit 708, a warning signal indicating that the distance d does not match the SID df. If the determining unit 712 is supplied with the response signal from the radiation source movement controller 706, then the determining unit 712 stops outputting the warning signal to the warning unit 708.

At the time the warning unit 708 is supplied with the warning signal from the determining unit 712, the warning unit 708 energizes a light-emitting diode (LED), for example, to emit light, indicating that the distance d does not match the SID df, to the surgeons 18 or the radiological technician in the operating room 12.

The radiation image capturing system 700 according to the third embodiment is basically constructed as described above, and operations of the radiation image capturing system 700 will be described below. Detailed explanations of the operations which are the same as those of the radiation image capturing systems 10, 600 shall be omitted.

After the above preparatory process is finished, the surgeons 18 or the radiological technician turns on the image capturing switch 80 of the radiation image capturing system 700 set in the operating room 12. Then, the radiation source controller 86 receives the image capturing conditions, and controls the signal detector 704 to detect the signals transmitted from the signal generators 702, supplies, to the determining unit 712, the SID df included in the image capturing conditions, and controls the determining unit 712 to compare the supplied SID df with the distance d.

The signal generators 702 are continuously or intermittently transmitting signals. Under the control of the radiation source controller 86, the signal detector 704 detects the signals transmitted from the signal generators 702, and outputs the detected signals to the distance calculator 710. The distance calculator 710 calculates the distance d based on the signals from the signal detector 704, and outputs the calculated distance d to the determining unit 712. Under the control of the radiation source controller 86, the determining unit 712 determines whether the distance d matches the SID df or not.

If the determining unit 712 judges that the distance d does not match the SID df, then the determining unit 712 outputs, to the warning unit 708, a warning signal indicating that the distance d does not match the SID df, and also outputs, to the radiation source movement controller 706, a control signal to equalize the distance d with the SID df.

Based on the warning signal from the determining unit 712, the warning unit 708 indicates, to the surgeons 18 or the radiological technician through LED light emission or the like, that the distance d does not match the SID df. Based on the control signal from the determining unit 712, the radiation source movement controller 706 controls the universal arms 30a, 30b to move the image capturing apparatus 22 to a predetermined position of the radiation source 82 where the distance d matches the SID df. After having moved the image capturing apparatus 22, the radiation source movement controller 706 outputs, to the determining unit 712, a response signal indicative of the completion of the movement of the image capturing apparatus 22.

Based on the response signal supplied to the determining unit 712, the determining unit 712 stops outputting the warning signal to the warning unit 708, and outputs the response signal to the radiation source controller 86. The warning unit 708 stops indicating, to the surgeons 18 or the radiological technician, that the distance d does not match the SID df. Further, based on the supplied response signal, the radiation source controller 86 controls the radiation source 82 to apply radiation X at a given dose to the patient 14 according to the image capturing conditions.

If the determining unit 712 judges that the distance d matches the SID df, then the determining unit 712 does not output the warning signal to the warning unit 708 or the control signal to the radiation source movement controller 706, but outputs, to the radiation source movement controller 706, a response signal indicating that the distance d matches the SID df. Based on the supplied response signal, the radiation source controller 86 starts the image capturing process by applying a radiation from the radiation source.

As described above, the radiation image capturing system 700 according to the third embodiment automatically detects the distance d between the radiation source 82 and the radiation detecting cassette 24 by the distance detecting unit 714, and automatically determines whether the distance d matches the SID df or not by the determining unit 712. With this system, it is possible to adjust the distance d into conformity with the SID df easily and highly precisely before capturing a radiation image. Thus, highly precise radiation image information can be obtained.

In the case where the surgeons 18 or the radiological technician manually operates the universal arms 30a, 30b to adjust the distance d before radiation image capturing, the distance d is detected automatically and whether the distance d matches the SID df or not is determined automatically. Thus, the burden on the surgeons 18 or the radiological technician can be remarkably lessened. Further, a radiation image can be captured efficiently.

In addition, according to the radiation image capturing system 700, in the case where the determining unit 712 determines that the distance d does not match the SID df, the radiation source movement controller 706 can automatically move the image capturing apparatus 22 by the universal arms 30a, 30b so as to the distance d matches the SID df. That is, the detection of the distance d, the determination whether the distance d matches the SID df or not, and the adjustment of the distance d into conformity with the SID df are performed automatically. Thus, the burden on the surgeons 18 or the radiological technician is further lessened, and the distance d and the SID df can be adjusted reliably and highly precisely. As a result, further more highly precise radiation image information can be obtained easily.

Although certain preferred embodiments of the present invention have been shown and described in detail, it should be understood that various changes and modifications may be made therein without departing from the scope of the appended claims.

What is claimed is:

1. A radiation image capturing system comprising:
   an image capturing unit including a radiation source for emitting a radiation;
   a cassette including a radiation conversion panel for detecting the radiation which has been emitted from said radiation source and which has passed through a subject, and converting the detected radiation into radiation image information;
   a position detecting unit for detecting respective positions of said radiation source and said radiation conversion panel; and
   a determining unit for determining whether said radiation source and said radiation conversion panel are placed in head-on facing relation to each other based on the positions of said radiation source and said radiation conversion panel which are detected by said position detecting unit;
   wherein said radiation source and said radiation conversion panel are separate from each other and movable with respect to each other,
   wherein said position detecting unit comprises a detector for detecting the respective positions of said radiation source and said radiation conversion panel in a horizontal plane, and
   wherein the detector comprises a first horizontal sensor for detecting a horizontal position of the radiation detecting cassette, a first vertical sensor for detecting a vertical position of the radiation detecting cassette, a second horizontal sensor for detecting a horizontal position of the image capturing unit, and a second vertical sensor for detecting a vertical position of the image capturing unit.

2. A radiation image capturing system according to claim 1, wherein said position detecting unit is mounted on said image capturing unit, said cassette, or a cassette holder for holding said cassette.

3. A radiation image capturing system according to claim 1, wherein said image capturing unit includes an actuating unit for moving said image capturing unit to a position which faces said radiation conversion panel head-on, and said actuating unit is energizable based on a determined result from said determining unit.

4. A radiation image capturing system according to claim 3, further comprising a warning unit for issuing a warning if said determining unit judges that said radiation source and said radiation conversion panel are not placed in head-on facing relation to each other based on the determined result from said determining unit.

5. A radiation image capturing system according to claim 3, wherein said detector comprises an azimuthal sensor for detecting a spatial position, a gravitational sensor, or an acceleration sensor for detecting an acceleration upon displacement of said cassette.

6. A radiation image capturing system according to claim 1, wherein an orientation detecting unit is mounted on said image capturing unit so as to face said cassette,
   said orientation detecting unit emits a light toward said cassette, and
   based on whether or not said orientation detecting unit detects a reflected light, said determining unit determines whether an irradiated surface of said cassette faces said radiation source.

7. A radiation image capturing system according to claim 1, wherein said determining unit determines whether a distance between said radiation source and said cassette detected by a distance detecting unit matches a predetermined distance between said radiation source and said cassette at a time of capturing a radiation image of the subject.

8. A radiation image capturing system according to claim 1, wherein the detector further comprises a first displacement sensor for detecting a displacement of the radiation detecting cassette and a second displacement sensor for detecting a displacement of the image capturing unit.

9. The radiation image capturing system according to claim 1, wherein the determining unit determines that said radiation source and the radiation conversion panel are placed in heads-on facing relation to each other when a center of the radiation source and a center of the radiation conversion panel are aligned with each other.

10. The radiation image capturing system according to claim 9, wherein the determining unit further determines that said radiation source and the radiation conversion panel are placed in heads-on facing direction when a distance between the radiation source and the radiation conversion panel is defined only by a single vertical distance.

11. The radiation image capturing system according to claim 3, wherein the determining unit determines that said radiation source and the radiation conversion panel are placed in heads-on facing relation to each other when a center of the radiation source and a center of the radiation conversion panel are aligned with each other, and when a distance between the radiation source and the radiation conversion panel is defined only by a single vertical distance.

* * * * *